United States Patent
Zhao et al.

(10) Patent No.: US 10,413,938 B2
(45) Date of Patent: Sep. 17, 2019

(54) CAPACITIVE MICROMACHINED ULTRASOUND TRANSDUCERS HAVING VARYING PROPERTIES

(71) Applicant: Kolo Medical, Ltd., San Jose, CA (US)

(72) Inventors: Danhua Zhao, San Jose, CA (US);
Xuefeng Zhuang, San Jose, CA (US);
Yongli Huang, San Jose, CA (US)

(73) Assignee: Kolo Medical, Ltd., San Jose, CA (US)

( * ) Notice: Subject to any disclaimer, the term of this patent is extended or adjusted under 35 U.S.C. 154(b) by 973 days.

(21) Appl. No.: 14/944,404

(22) Filed: Nov. 18, 2015

(65) Prior Publication Data
US 2017/0136495 A1    May 18, 2017

(51) Int. Cl.
| | | |
|---|---|---|
| *B06B 1/02* | (2006.01) | |
| *A61B 8/00* | (2006.01) | |
| *A61B 8/08* | (2006.01) | |
| *G01S 15/89* | (2006.01) | |

(52) U.S. Cl.
CPC ............. *B06B 1/02* (2013.01); *A61B 8/52* (2013.01); *B06B 1/0292* (2013.01); *G01S 15/895* (2013.01); *G01S 15/8915* (2013.01); *G01S 15/8927* (2013.01); *A61B 8/4494* (2013.01); *A61B 8/5207* (2013.01)

(58) Field of Classification Search
CPC ..... B06B 1/02; B06B 1/0292; G01S 15/8927; G01S 15/8915; G01S 15/895; A61B 8/52; A61B 8/5207; A61B 8/4494
See application file for complete search history.

(56) References Cited

U.S. PATENT DOCUMENTS

| | | |
|---|---|---|
| 7,564,172 B1 | 7/2009 | Huang |
| 7,612,635 B2 | 11/2009 | Huang |
| 7,759,839 B2 | 7/2010 | Huang |
| 7,764,003 B2 | 7/2010 | Huang |
| 7,779,696 B2 | 8/2010 | Huang |
| 7,880,565 B2 | 2/2011 | Huang |
| 7,956,510 B2 | 6/2011 | Huang |
| 8,004,373 B2 | 8/2011 | Huang |
| 8,008,105 B2 | 8/2011 | Huang |
| 8,018,301 B2 | 9/2011 | Huang |
| 8,105,941 B2 | 1/2012 | Huang |
| 8,120,229 B2 | 2/2012 | Huang |
| 8,247,945 B2 | 8/2012 | Huang |

(Continued)

FOREIGN PATENT DOCUMENTS

CN            106694347 A  *  5/2017  ............... A61B 8/52

*Primary Examiner* — Daniel Pihulic
(74) *Attorney, Agent, or Firm* — Mattingly & Malur, PC

(57) ABSTRACT

In some examples, a CMUT array may include a plurality of elements, and each element may include a plurality of sub-elements. For instance, a first sub-element and a second sub-element may be disposed on opposite sides of a third sub-element. In some cases, the third sub-element may be configured to transmit ultrasonic energy at a higher center frequency than at least one of the first sub-element or the second sub-element. Further, in some instances, the sub-elements may have a plurality of regions in which different regions are configured to transmit ultrasonic energy at different resonant frequencies. For instance, the resonant frequencies of a plurality of CMUT cells in each sub-element may decrease in an elevation direction from a center of each element toward the edges of the CMUT array.

29 Claims, 17 Drawing Sheets

(56) References Cited

U.S. PATENT DOCUMENTS

| | | |
|---|---|---|
| 8,345,513 B2 | 1/2013 | Huang |
| 8,363,514 B2 | 1/2013 | Huang |
| 8,429,808 B2 | 4/2013 | Huang |
| 8,483,014 B2 | 7/2013 | Huang |
| 8,526,271 B2 | 9/2013 | Huang |
| 8,559,274 B2 | 10/2013 | Huang |
| 8,767,514 B2 | 7/2014 | Huang |
| 8,796,901 B2 | 8/2014 | Huang |
| 8,815,653 B2 | 8/2014 | Huang |
| 8,926,517 B2 | 1/2015 | Huang |
| 8,952,595 B2 | 2/2015 | Huang |
| 8,975,984 B2 | 3/2015 | Huang |
| 9,132,450 B2 | 9/2015 | Huang |
| 9,221,077 B2 | 12/2015 | Chen et al. |
| 9,408,588 B2 | 8/2016 | Huang |
| 2010/0246332 A1* | 9/2010 | Huang ............... A61B 8/06 367/181 |
| 2017/0136495 A1* | 5/2017 | Zhao ............... A61B 8/52 |

* cited by examiner

CAPACITIVE MICROMACHINED ULTRASOUND TRANSDUCERS HAVING VARYING PROPERTIES

TECHNICAL FIELD

Some examples herein relate to capacitive micromachined ultrasound transducers (CMUTs), such as may be used for ultrasound imaging.

BACKGROUND

Ultrasound transducers are widely used in many different fields including ultrasound imaging. In many modern medical imaging applications, ultrasound transducers are made of piezoelectric materials. One commonly used piezoelectric material is lead zirconate titanate (PZT). However, the impedance of PZT is usually higher than 30 MRayls while the impedance of human tissues is around 1.5 MRayls. In order to reduce this huge impedance mismatch, one or more matching layers are often placed between the PZT transducer and the tissue being imaged. Since the matching layers are typically selected based on the one-quarter-wavelength principle, the bandwidth of PZT transducers having matching layers may be limited to 80% or less bandwidth.

Traditionally, ultrasound transducers are arranged in one-dimensional (1D) arrays. For example, a 1D array transducer may include multiple elements arranged in only one dimension, e.g., the lateral dimension. In another dimension, e.g., the elevation dimension, however, the aperture of a 1D transducer is fixed. Since the aperture size is increased with penetration depth to maintain uniform elevation slice thickness, the imaging performance of a 1D transducer is compromised due to its fixed elevation aperture. One solution to this problem is to use a 1.5D transducer array. For example, a 1.5D transducer array may include at least two sub-elements in the elevation dimension. The spacing between the two adjacent sub-elements may be much larger than the wavelength. Further, the number of sub-elements may increase with penetration depth for optimal imaging performance from near field to far field. The number of elements and sub-elements of 1.5D arrays is usually significantly larger than the number of channels of the respective imaging systems. Therefore, high voltage analog switches may be used for selecting desired sub-apertures of 1.5D arrays.

SUMMARY

Some implementations herein include techniques and arrangements for capacitive micromachined ultrasonic transducers (CMUTs) able to be used for various applications including ultrasound imaging. For example, the center frequency associated with individual CMUT elements in a CMUT array may decrease from a center of the CMUT array toward the edges due to variations in the properties of the CMUT cells making up the individual CMUT elements. Accordingly, in some cases, an ultrasound system herein may include multiple sub-elements for enabling an ultra-wide bandwidth, variable pitch, and/or continuous elevation apodization.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
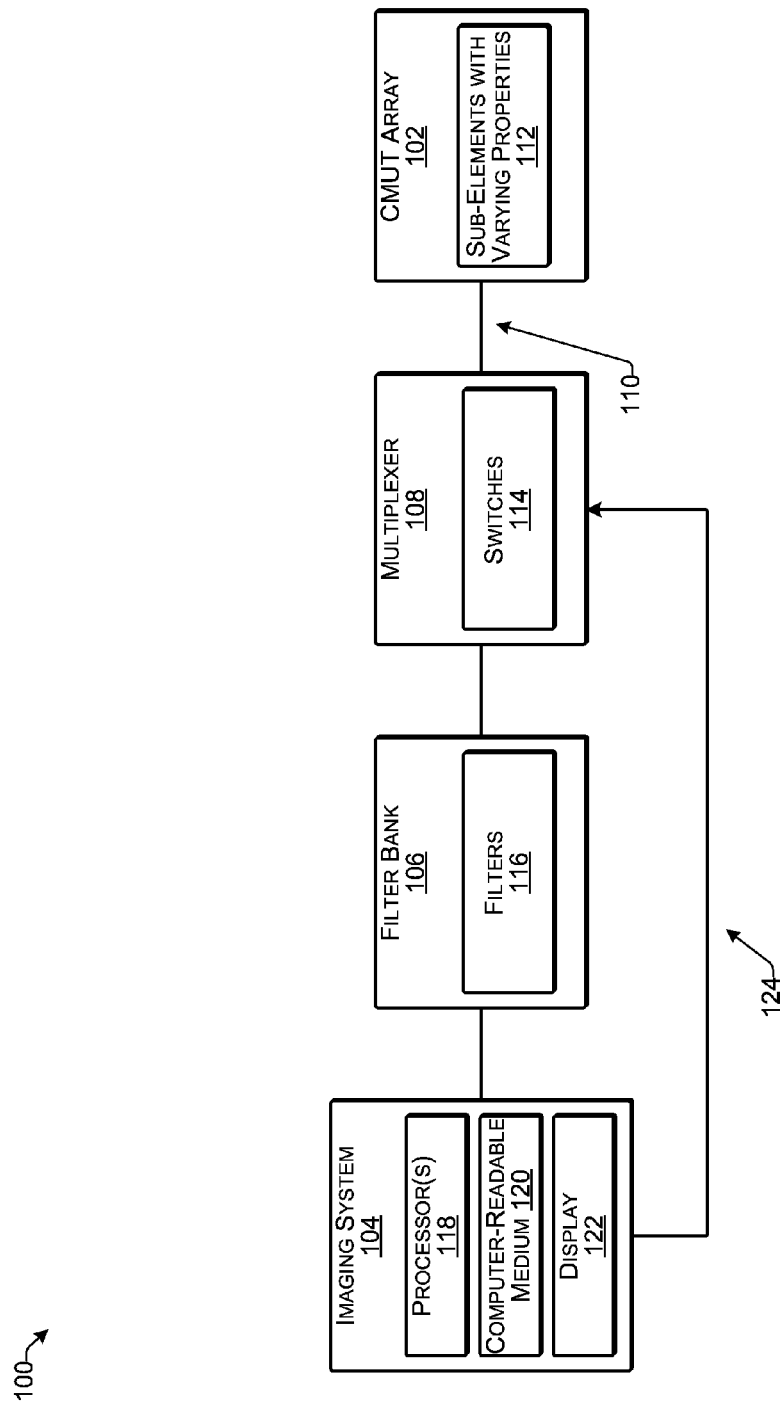
FIG. 1 illustrates an example ultrasound imaging system with a CMUT array according to some implementations.

Some implementations herein include techniques and arrangements for CMUTs able to be used for various ultrasound applications, including ultrasound imaging. The CMUT transducers herein are able to operate without matching layers and therefore may operate with extremely wide bandwidths, e.g., greater than or equal to 100 percent. As one example, a CMUT array according to some implementations herein may have more than two sub-elements in an elevation dimension, such as in the case of 1.25D, 1.5D, 1.75D, and 2D CMUT transducers arrays. For instance, in the examples herein, a 1.5D array may include a CMUT array that has more than two sub-elements in the elevation dimension, with some of the sub-elements being electrically connected to each other.

Some implementations herein are applicable to CMUT arrays able to be used for ultrasound imaging, such as for medical imaging applications. As one example, a disclosed versatile CMUT array having multiple sub-elements may be used for a wide range of clinical applications by providing ultra-wide bandwidth, variable pitch, continuous elevation apodization, and variable aperture size. For instance, an ultra-wide bandwidth may be achieved by varying properties of individual CMUT cells on the transducer elements. Further, high voltage analog switches may be used in some cases to change a pitch for various operating frequencies. In addition, a continuous elevation apodization may be realized by applying different bandpass filters to transmitted and received signals. In some examples, the CMUTs herein may be incorporated into an ultrasound probe able to be used for ultrasound imaging applications.

The center frequency and transducing efficiency are two useful performance parameters for a CMUT. The center frequency may also be referred to as a −6 dB center frequency. If the lower frequency limit of −6 dB bandwidth is $f_{low}$ and the upper frequency limit of −6 dB bandwidth is $f_{high}$, then the center frequency is $(f_{low}+f_{high})/2$. In some cases, the center frequency can be also defined by −10 dB or −20 dB bandwidth. No matter which definition, usually the center frequency is determined by the resonant frequency of a CMUT cell structure (e.g., the resonant frequency of a membrane over a cavity in a CMUT cell). The higher the resonant frequency of a CMUT cell structure, then the higher the center frequency. A CMUT can be used to transmit (TX) acoustic power into a medium, or to receive (RX) an acoustic signal from the medium, or both.

Furthermore, in implementations herein, transducing efficiency may include the CMUT transmission efficiency, receiving sensitivity, or both (i.e., loop sensitivity). For example, both the transmission efficiency and the receiving sensitivity may be determined by the intensity of the electrical field within the transducing space (i.e., the gap between two electrodes of a CMUT including the CMUT cavity). A higher electrical intensity results in a higher transmission efficiency and a higher receiving sensitivity. For a given applied voltage, such as a bias voltage, the electrical intensity in the transducing space may be determined by the cavity dimensions (e.g., depth, shape, profile, etc.).

For discussion purposes, some example implementations are described in the environment of ultrasound imaging. However, implementations herein are not limited to the particular examples provided, and may be extended to other applications, other systems, other environments for use, other array configurations, and so forth, as will be apparent to those of skill in the art in light of the disclosure herein.

FIG. 1 illustrates an example ultrasound imaging system 100 including a CMUT array according to some implementations. In this example, the system 100 includes a CMUT array 102. In some cases, the CMUT array 102 may be a 1.5D CMUT array having more than two sub-elements in the elevation dimension as discussed additionally below. The system 100 further includes an imaging system 104, a filter bank 106, and a multiplexer 108 in communication with the CMUT array 102. In some examples, the system 100 may include, or may be included in, an ultrasound probe for performing ultrasound imaging. Further, the system 100 may include multiple transmit and receive channels 110. As one example, the CMUT array 102 may include 128 transmit and receive channels 110 that communicate with the multiplexer 108. In addition, the CMUT array 102 may include N×M sub-elements 112, e.g., where N is the number of elements, and M is the number of sub-elements for each element along elevation direction. In some examples, the properties of at least some of the sub-elements 112 may vary, and in some cases, the properties of CMUT cells within the sub-elements 112 may vary.

In some instances, the multiplexer 108 may include a large number of switches 114, which may be high voltage analog switches in some cases. Further, the filter bank 106 may include multiple filters 116 for both transmit and receive channels. At least some of the filters 116 may be bandpass filters and the filters 116 may be analog or digital.

The imaging system 104 may include one or more processors 118 and a computer-readable medium 120. For example, the processor(s) 118 may be implemented as one or more microprocessors, microcontrollers, digital signal processors, logic circuits, and/or other devices that manipulate signals based on operational instructions. The computer-readable medium 120 may be a tangible non-transitory computer storage medium and may include volatile and nonvolatile memory, computer storage devices, and/or removable and non-removable media implemented in any type of technology for storage of information such as signals received from the CMUT array 102 and/or processor-executable instructions, data structures, program modules, or other data. Further, when mentioned herein, non-transitory computer-readable media exclude media such as energy, carrier signals, electromagnetic waves, and signals per se.

In some examples, the imaging system 104 may include, or may be connectable to a display 122 and/or various other input and/or output components such as for visualizing the signals received by the CMUT array 102. Furthermore, as indicated at 124, the imaging system 104 may communicate directly with the multiplexer 108 in some cases, such as for controlling the switches 114, in addition to communicating with the filter bank 106.

Figure 2:
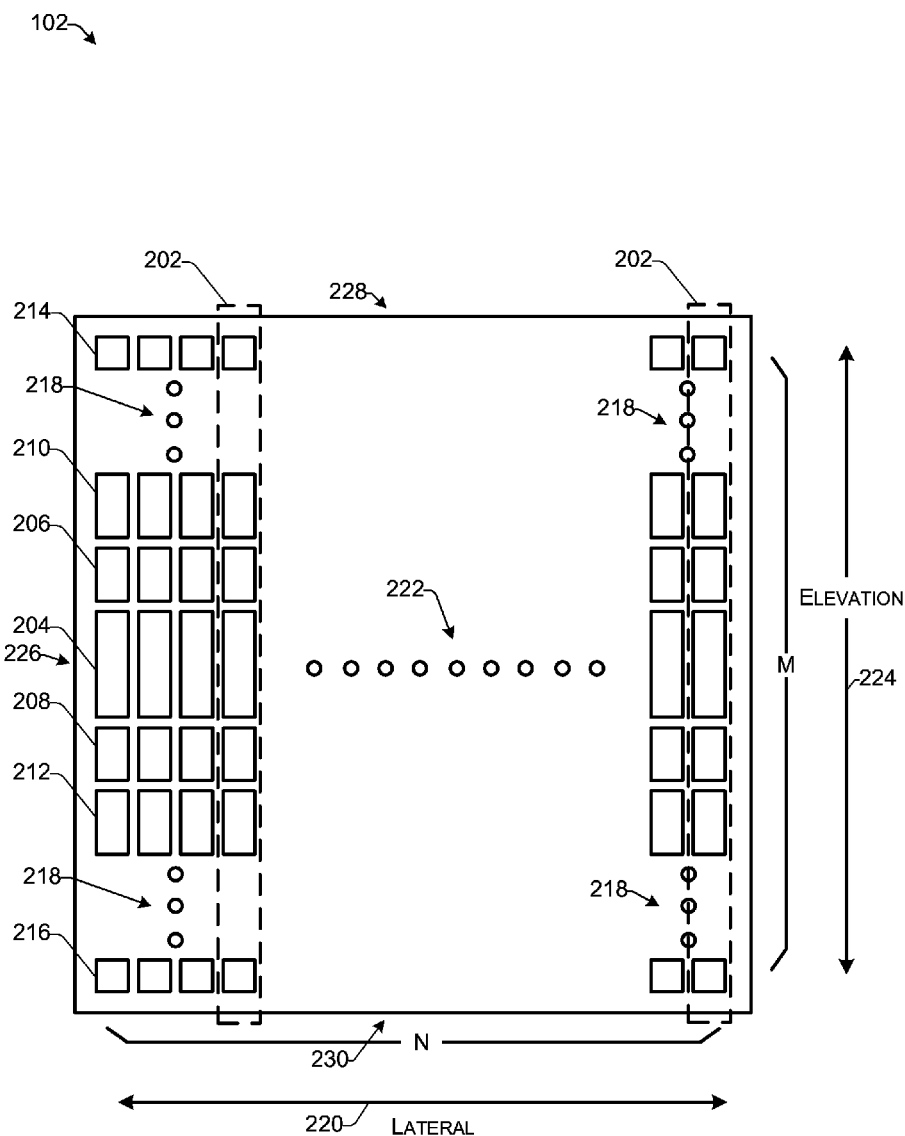
FIG. 2 illustrates an example structure of a CMUT array according to some implementations.

FIG. 2 illustrates a plan view of an example configuration of a CMUT array 102 according to some implementations. In some examples, the CMUT array 102 may be a 1.5D CMUT array that includes N×M sub-elements. As illustrated, the CMUT array 102 includes a plurality of elements 202. Each element 202 includes M sub-elements 204, 206, 208, 201, 212, 214, 216, . . . . The properties of the respective sub-elements 204-216, such as size, shape, frequency ranges, etc., may be designed to be similar or different from others of the sub-elements 204-216. Further, in some examples, additional sub-elements may be included in each element 202, as indicated by dots 218.

In the illustrated example, the sub-elements in each individual element 202 are arranged symmetrically about a center sub-element 204. Accordingly, the sub-elements 206 and 208 may have the same or similar properties, the sub-elements 210 and 212 may have the same or similar properties, and sub-elements 214 and 216 may have the same or similar properties. Moreover, in the most cases, the symmetrical sub-elements 206 and 208, 210 and 212, and 214 and 216 are electrically connected together as a pair, e.g., sub-element 206 and sub-element 208 may be electrically connected together, sub-element 210 and sub-element 212 may be electrically connected together, sub-element 214 and sub-element 216 may be electrically connected together, and so forth. As one example, the bottom electrodes and top electrodes of two paired sub-elements may be electrically connected to each other. For instance, the paired sub-elements may be electrically connected so that a transmission signal is delivered concurrently through the two electrically connected sub-elements. Similarly, reflected ultrasonic energy may be received concurrently through the two electrically connected sub-elements.

As mentioned above, in a lateral direction 220, there are N elements 202. As indicated by dots 222, the number of elements 202 may depend at least in part on a desired size of the CMUT array 102. Additionally, in an elevation direction 224, there are M sub-elements in each element 202. In some examples, when there is a larger number M of sub-elements included in the elements 202 of the CMUT array 102, the aperture of the CMUT array 102 is larger than when there are fewer sub-elements included in elements 202 of the CMUT array 102. In some examples, the aperture of the CMUT may be controlled to change dynamically. Thus, an aperture size may be made larger in the elevation direction by using a larger number of sub-elements 206-218 in the array 102 to transmit and/or receive ultrasonic energy as traveling time or depth increases in real-time during receive phase.

The dynamic elevation aperture growth allows the imaging system to maintain a high image quality throughout display depth from near field to far field. Having a larger aperture size may enable imaging at greater depths in a medium. The ratio of the imaging depth to the aperture size is known as the F-number. In addition, the sizes or other properties of the sub-elements may be designed so that the elevation aperture grows at a constant rate or the F-number remains a constant. Alternatively, the elevation aperture may be increased at a constant percentage rate. For instance, the aperture growth rate may be more than 100% for M=3, 50% for M=5, 25-33% for M=7, etc. In some cases, such as when the number of sub-elements M is less than 5, the center sub-element 204 may be longer in the elevation direction 224 than the length of the other sub-elements 206-218 in the elevation direction 224. For instance, in the illustrated example, the center sub-element 204 may be approximately twice as long as adjacent sub-elements 206 and 208.

Operating frequencies may be closely controlled in medical ultrasound imaging applications. On one hand, it is desirable to have higher operating frequencies because this can produce better imaging resolution; other the other hand, it might be more desirable to use lower operating frequencies due to obtain deeper penetration of the ultrasonic energy. Some examples herein address these conflicting goals by utilizing sub-elements that have different center frequencies. Since near-field imaging may employ a small elevation aperture, it may be desirable to have a center sub-element that has a higher center frequency. As the imaging depth increases, however, a larger elevation aperture and a lower center frequency may be employed. Therefore, in implementations herein, the center frequency of edge sub-elements decreases from a center 226 toward both edges 228, 230 of the array 102.

In some implementations herein, the center frequency of respective sub-elements 204-218 may be different from the center frequency of other respective sub-elements 204-218. For instance, the center frequency of the sub-elements closer to a center 226 in the elevation direction 224 of the CMUT array 102 is higher than the center frequency of the sub-elements closer to the upper edge 228 and lower edge 230 of the CMUT array 102. For example, the center frequency of the central sub-element 204 may be higher than that of sub-elements 206 and 208. Further, the center frequency of sub-elements 206 and 208 may be higher than that of sub-elements 210 and 212, respectively, and so forth.

Figure 3:
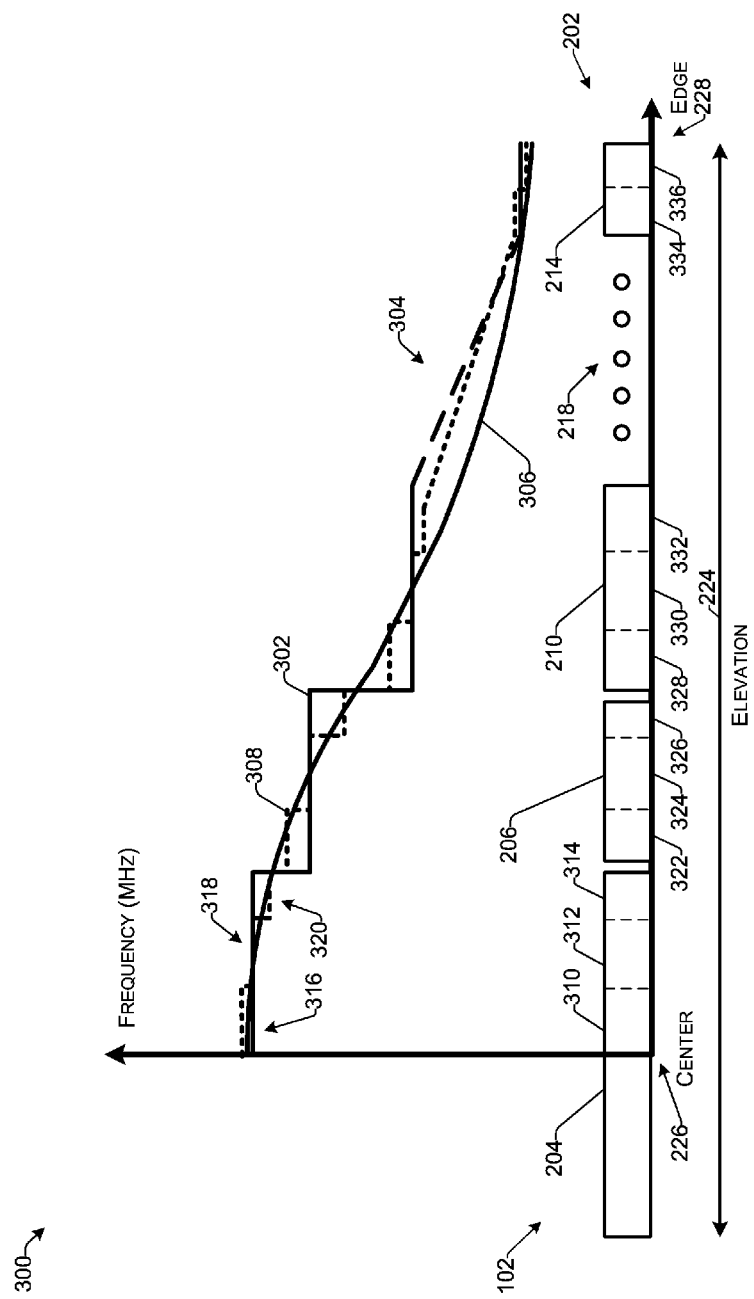
FIG. 3 is an example graph illustrating one example of how the center frequency may vary in the elevation direction according to some implementations.

FIG. 3 is a graph 300 illustrating an example of how the center frequency may change in the elevation direction according to some implementations. In this example, the center frequency may be a monotonically decreasing function and may change in the elevation direction 224 from the center 226 of the CMUT array 102 to the edge 228. In some cases, the center frequency may change similarly from the center 226 toward the other edge 230 of the CMUT array 102, such as in a mirror image of the graph 300 (not shown in FIG. 3). The graph 300 includes an example solid stepped line 302 representing decreases in frequency of one half of a CMUT element 202 from the center 226 toward the edge 228. The stepped line 302 shows that each sub-element 204, 206, 210, 218, and 214 may have a different center frequency from others of the sub-elements 204, 206, 210, 218, and 214. In this example, the stepped line frequency representation 302 shows that the center sub-element 204 has the highest center frequency, and the stepped line 302 decreases successively at each next respective sub-element 206, 210, and 214 based on the center frequency of the respective sub-elements 206, 210, and 214 decreasing toward the edge 228. Further, the stepped line 302 is shown having a dashed line at 304 corresponding to the sub-elements 218. As mentioned above, the sub-elements 218 may include any number of additional sub-elements in some examples, and may also decrease progressively toward the edge 228.

The graph 300 further illustrates a solid lined curve 306, which may represent an ideal example frequency curve in the elevation direction 224 for the CMUT element 202. In general, the frequency curve 306 is a monotonically decreasing function from the center 226 to the edge 228 that is approximated by the stepped changes in center frequency from one sub-element 204-210 to the next sub-elements 206-214, respectively. For instance, the frequency curve 306 may be a Gaussian function or a Kaiser-window-like Hamming window. Thus, the changes in frequency from one sub-element 204-218 to the next may be configured to approximate the ideal frequency curve 306.

Furthermore, in some examples, as indicated by a dotted stepped line 308, the individual sub-elements 204-218 herein may be designed to have different regions within each sub-element that produce different center frequencies. Having individual sub-elements 204-214 with different regions having different center frequencies may enable the CMUT element 202 to more closely approximate the ideal frequency curve 306. For instance, the sub-element 204 may include regions 310, 312, and 314, each of which may be configured to have a different center frequency as shown by the stepped portions 316, 318, and 320, respectively of the dotted stepped line 308. Similarly, in this example, the sub-element 206 includes three regions 322, 324, and 326 having successively decreasing frequencies, the sub-element 210 has three regions 328, 330, and 332 having successively decreasing frequencies, and the sub-element 214 has two regions 334 and 336, where the region 336 has a lower center frequency than the region 334.

Figure 4:
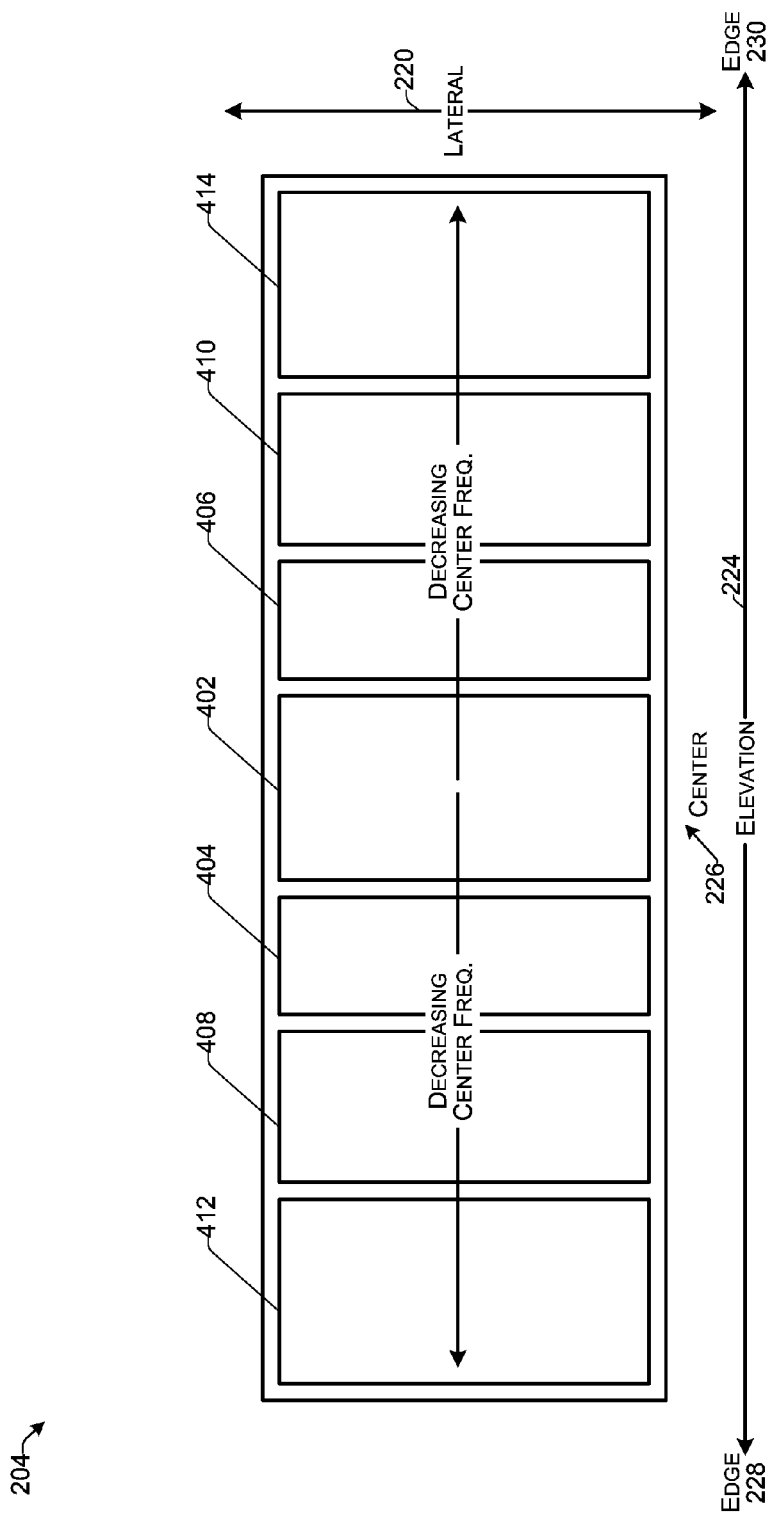
FIG. 4 illustrates a plan view of an example configuration of a center sub-element according to some implementations.

FIG. 4 illustrates a plan view of an example of the center sub-element 204 according to some implementations. In this example, the center sub-element 204 includes a plurality of regions, e.g., a center region 402, and regions 404, 406, 408, 410, 412, and 414. The center frequency associated with the center region 402 may be higher than the center frequency associated with the regions 404 and 406. The center frequency associated with the regions 404 and 406 may be higher than the center frequency associated with the regions 408 and 410, respectively. The center frequency associated with the regions 408 and 410 may be higher than the center frequency associated with the regions 412 and 414, respectively. Thus, the center frequencies of the regions 402-414 decrease successively and symmetrically in the elevation direction 224 from the center 226 toward the edges 228 and 230. As discussed additionally, below, each of the regions 402-414 may be made up of one or more individual CMUT cells having different frequency properties from CMUT cells of others of the regions 402-414.

Figure 5:
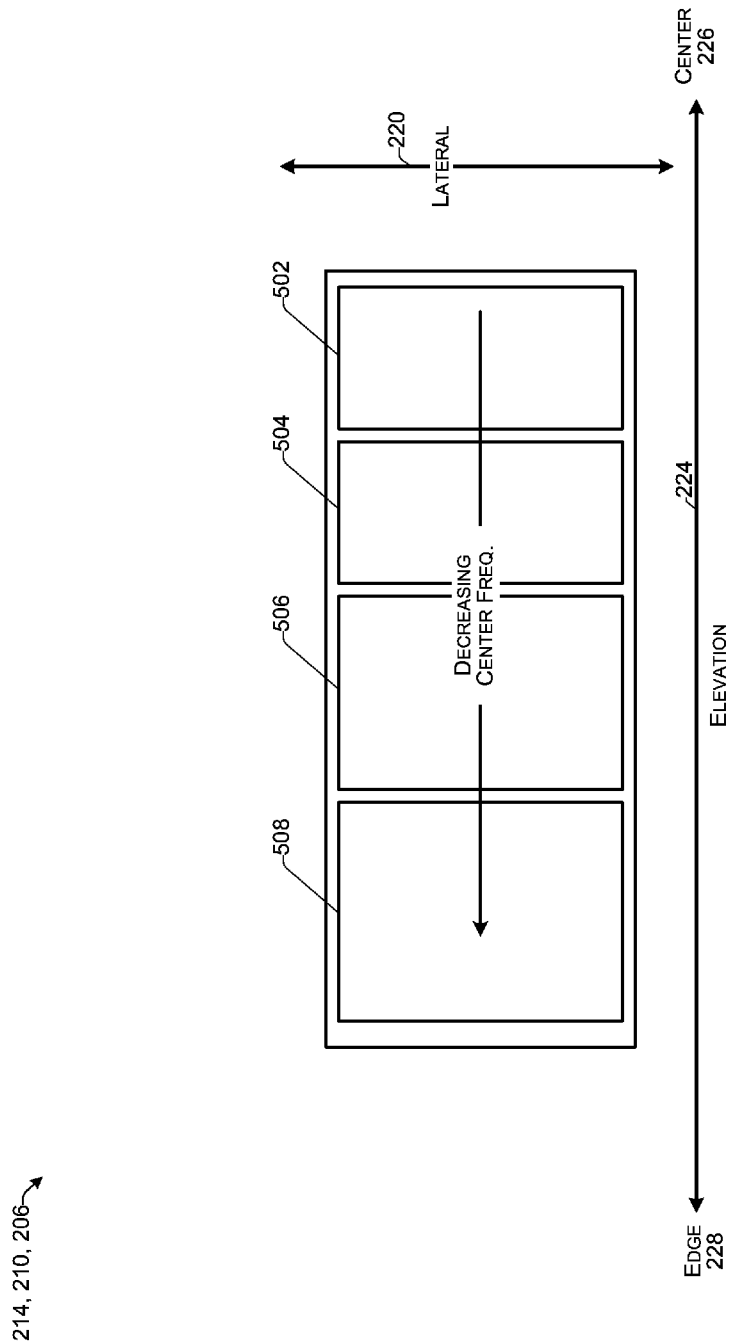
FIG. 5 illustrates a plan view of an example configuration of a sub-element having multiple regions with different center frequencies according to some implementations.

FIG. 5 illustrates a plan view of an example configuration of the sub-elements 206, 210, 214 having multiple regions with different center frequencies according to some implementations. In this example, the sub-elements 206, 210, and/or 214 may each include a plurality of regions, such as regions 502, 504, 506, and 508. The center frequency associated with the region 502 may be higher than the center frequency associated with the region 504. The center frequency associated with the region 504 may be higher than the center frequency associated with the region 506. The center frequency associated with the region 506 may be higher than the center frequency associated with the region 508. Thus, the center frequencies of the regions 502-508 decrease successively in the elevation direction 224 from the center 226 toward the edge 228. Sub-elements 208, 212, and/or 216 of FIG. 2 may be similarly configured in a mirror image to decrease in center frequency toward the edge 230 (not shown in FIG. 5).

Figure 6:
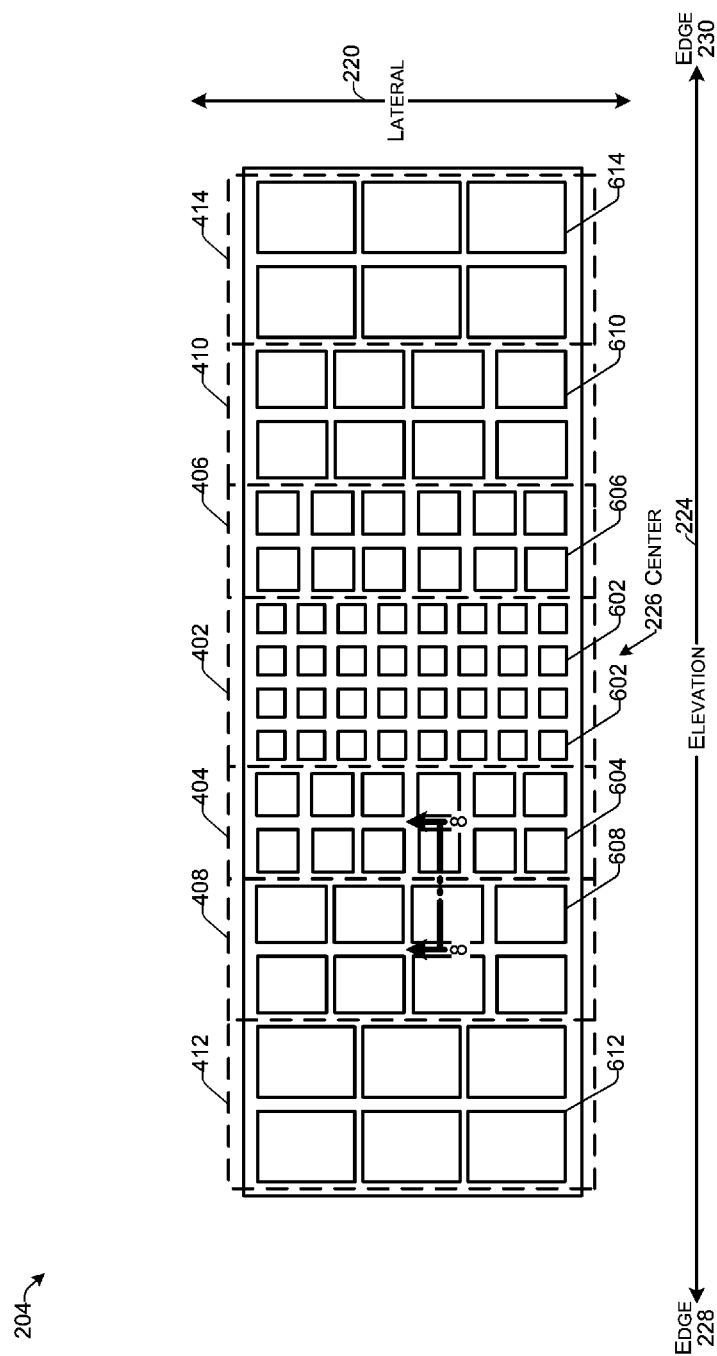
FIG. 6 illustrates a plan view of an example configuration of a center sub-element according to some implementations.

FIG. 6 illustrates a plan view of a configuration of the example center sub-element 204 according to some implementations. In this example, the center sub-element 204 includes the regions 402-414, as discussed above with respect to FIG. 4. Each region 402-414 may be made up of one or more individual CMUT cells. For instance, different from a PZT transducer, each CMUT element or sub-element may be made of multiple CMUT cells. By using different CMUT cells having different properties (e.g., transducing efficiency, frequency, etc.) in each region 402-414 of the sub-element 204, implementations herein enable construction of a CMUT sub-element having different center frequencies in different sub-elements and in different regions in the different sub-elements.

In some examples, the CMUT cells herein may have a membrane vibration structure that vibrates at a designed resonant frequency. For instance, the center frequency of a CMUT cell may be controlled at least in part by the mechanical properties of a vibration structure of the CMUT cell. For a CMUT cell having a vibration membrane, the center frequency may be configured based on the resonant frequency of the membrane, such as the first resonant frequency of the membrane. As one example, as discussed additionally below, if the thickness of the membrane of the CMUT cell is uniform, the resonant frequency of the CMUT cell may correspond to the dimensions of the membrane of the CMUT cell in the lateral and elevation directions, i.e., the dimension of the membrane is defined by the dimension of a cavity of the CMUT cell underneath the membrane. Furthermore, the types of CMUT cells that may be used in implementations herein are not limited to those shown in some examples, but may be extended to other types of CMUT cells, as will be apparent to those of skill in the art having the benefit of the disclosure herein.

In the example of FIG. 6, square/rectangular CMUT cells are used as the exemplary CMUT cells, and the dimensions of the CMUT cells (e.g., moveable membrane area overlying the cavity area when viewed in plan, as in FIG. 6) increases in the elevation dimension 224 from the center 226 toward the edges 228, 230. The dimension of the membrane size is defined by the cavity size underneath the membrane. In this example, a plurality of CMUT cells 602 in the center region 402 may be smaller in size, when viewed in plan, than a plurality of CMUT cells 604 in the region 404 and a plurality of CMUT cells 606 in the region 406, i.e., based on comparison of the dimension the respective CMUT cell cavity. For instance, since the membrane of each cell 602 extends across a cavity having a smaller dimension than the dimensions of the cavities of each CMUT cell 604 and 606, the CMUT cells 602 may have a higher resonant frequency, then also a higher center frequency, than the CMUT cells 604 and 606, assuming that the membrane thickness is constant.

Similarly, the region 408 includes a plurality of CMUT cells 608 having membranes that are larger in area than the membranes of the CMUT cells 604, or otherwise have a lower resonant frequency; and the region 410 includes a plurality of CMUT cells 610 having membranes that are larger in area than the membranes of the CMUT cells 606, or otherwise have a lower resonant frequency, also a lower center frequency. The region 412 includes a plurality of CMUT cells 612 having membranes that are larger in area than the membranes of the CMUT cells 608, or otherwise have a lower resonant frequency; and the region 414 includes a plurality of CMUT cells 614 having membranes that are larger in area than the membranes of CMUT cells 610, or otherwise have a lower resonant frequency. Thus, by increasing the size, e.g., the area of the membranes when viewed in plan, of the CMUT cells from the center 226 in the elevation direction toward the edges 228, 230, the resonant frequency and thereby the center frequency of the respective regions 402-414 may decrease as discussed above with respect to FIGS. 3 and 4.

Additionally, or alternatively, rather than having square or otherwise rectangular shaped CMUT cells when viewed in plan, as shown in FIG. 6, the CMUT cells 602-614 may have membranes (cavities) of various other shapes or any combination of shapes such as hexagonal, circular, triangular, trapezoidal, and so forth.

As still another alternative, rather than varying the dimensions of the cell cavities (membranes), the thickness (or thickness profile if the membrane is not uniform) of the membrane may be varied to change the resonant frequency of the CMUT cells, or combinations of different membrane thicknesses, thickness profiles and/or different cell cavity sizes may be used in some examples for varying the resonant frequencies of the CMUT cells 604-614. Further, in other examples, the membrane thickness profile (the membranes may be weighted, structured, or otherwise patterned) may be designed to control the resonance properties of the respective membranes of the CMUT cells in the different regions 402-414.

Figure 7:
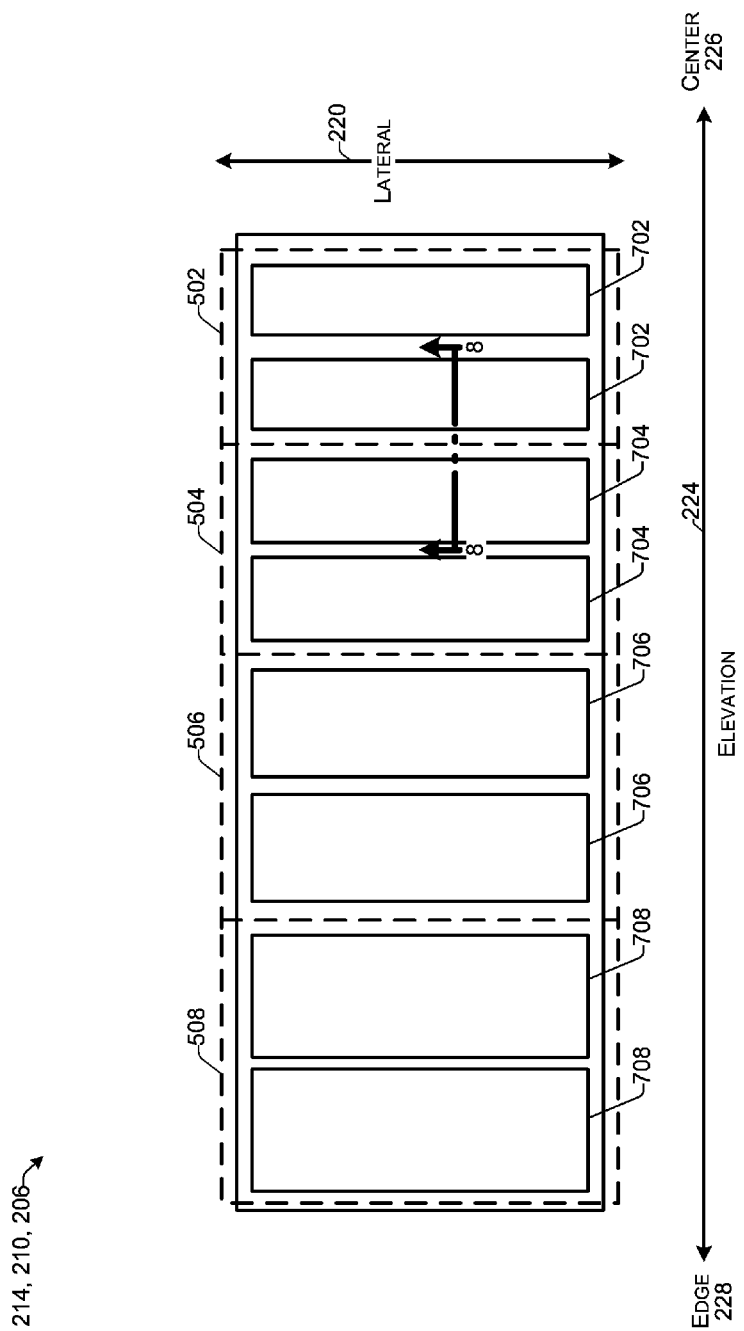
FIG. 7 illustrates a plan view of an example configuration of a sub-element according to some implementations.

FIG. 7 illustrates a plan view of an example configuration of the sub-elements 206, 210, and 214 of FIG. 5 according to some implementations. For instance, the sub-elements 206, 210, and/or 214 may have multiple regions with different center frequencies. In this example, each region 502, 504, 506, and 508 includes at least one rectangular CMUT cell. Thus, the region 502 includes CMUT cells 702, the region 504 includes CMUT cells 704 having a resonant frequency less than that of the CMUT cells 702, the region 506 includes CMUT cells 706 having a resonant frequency less than that of the CMUT cells 704, and the region 508 includes CMUT cells 708 having a resonant frequency less than that of the CMUT cells 706. Accordingly, the center frequency of the regions 502, 504, 506, and 508 may decrease in the elevation dimension 224 from the center 226 toward the edge 228 as the dimension of the short side of the rectangular CMUT cell membranes increase, respectively. Further, as mentioned above with respect to FIG. 5, in some examples, the sub-elements 208, 212, and 216 may be mirror images of the sub elements 206, 210, and 214 respectively. In addition, some of the sub-elements 206, 210, 214 may include more or fewer regions having different center frequencies.

Figure 8:
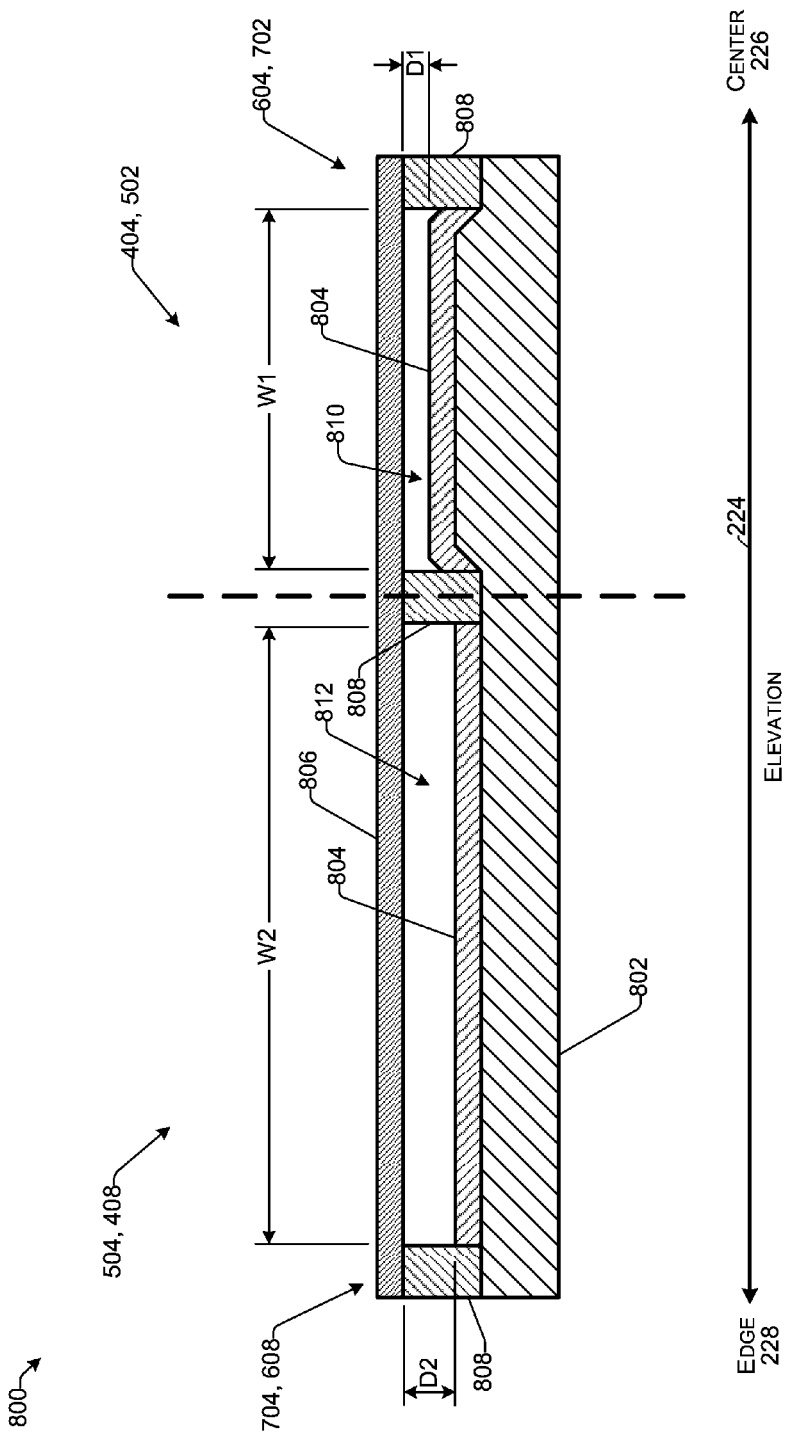
FIG. 8 illustrates an example cross-sectional view as viewed along line 8-8 of FIG. 6 and/or line 8-8 of FIG. 7 according to some implementations.

FIG. 8 illustrates an example cross-sectional view 800 as viewed along line 8-8 of FIG. 6 and/or line 8-8 of FIG. 7 according to some implementations. In this example, a first CMUT cell 604 or 702 and an second CMUT cell 606 or 704, respectively, are formed on a common substrate 802. In some examples, the substrate 802 may be formed of a conductive material and may serve as a common first or bottom electrode for both the first CMUT cell 604 or 702, and the second CMUT cell 606 or 704, respectively. In other examples, such as in the case that the substrate is formed of a nonconductive material, a layer of conductive material (not shown in FIG. 8) may be deposited onto an upper surface of the substrate 802 to serve as the bottom electrode, such as prior to deposition of an optional insulation layer 804. Further, the two CMUT cells illustrated in FIG. 8 may not necessary be adjacent cells. The relationship between the two cells may generally be described as: a first CMUT cell with higher frequency is closer to the center 226 of the CMUT array, and a second CMUT cell with lower frequency is closer to the edge 228 of the CMUT array (or edge 230 in other examples).

A membrane 806 may be disposed over the substrate 802 and may be supported by sidewalls 808 to provide a first cavity 810 for the first CMUT cell 604 or 702, and a second cavity 812 for the second CMUT cell 606 or 704, respectively. In the illustrated example, the membrane 806 has a uniform thickness over both the first cavity 810 and the second cavity 812. The membrane 806 may be made of single layer or multiple layers, and at least one layer may be of a conductive material to enable the membrane 806 to serve as a second or upper electrode. The portion of the membrane 806 disposed over the first cavity 810 has a smaller width W1 than the width W2 of a portion of the membrane 806 disposed over the second cavity 812. Thus, as illustrated above with respect to FIGS. 6 and/or 7, the moveable portion the membrane 806 disposed over the first cavity 810 has a smaller area than the moveable portion of the membrane 806 disposed over the second cavity 812. For example, as illustrated in FIGS. 6 and 7, the first CMUT cell 604 or 702, has a lateral length that is less than or equal to the lateral length of the second CMUT cell 606 or 704, respectively. Consequently, the resonant frequency of the first CMUT cell 604 or 702, having the cavity 810 is higher than the resonant frequency of the second CMUT cell 606 or 704, respectively, having the cavity 812. Accordingly, by changing the dimensions of the cavities (membranes) (e.g., when viewed in plan, as in FIGS. 6 and 7, or when viewed in cross section, as in FIG. 8), the central frequencies of the respective CMUT cells may vary from the first CMUT cell 604 or 702 to the second CMUT cell 606 or 704, respectively, to achieve the frequency profile described with respect to FIG. 3.

Alternatively, in some examples, the thickness of the membrane 806 is not uniform over the cavities 810 and 812. For instance, instead of changing the dimensions of the membrane 806 and the dimensions of the cavities 810, 812, the membrane thickness profile may be different over different CMUT cells, while the widths W1 and W2 and lengths in the lateral direction of the cavities 810 and 812 may be the same. Accordingly, forming successively thinner membrane thicknesses or more flexible membranes over CMUT cells in the elevation direction toward the edges 228 and 230 may also be used to achieve the frequency profile shown in FIG. 3. One example of CMUT cells having non-uniform membrane thicknesses is shown in FIG. 9.

In addition, the first CMUT cell 604, 702 may have a smaller depth D1, than a depth D2 of the second CMUT 608, 704. This difference in depth may also contribute to a difference in transducing efficiency between the first CMUT cell 602, 702, and the second CMUT cell 608, 704, respectively, as discussed additionally below with respect to FIGS. 10 and 11.

Figure 9:
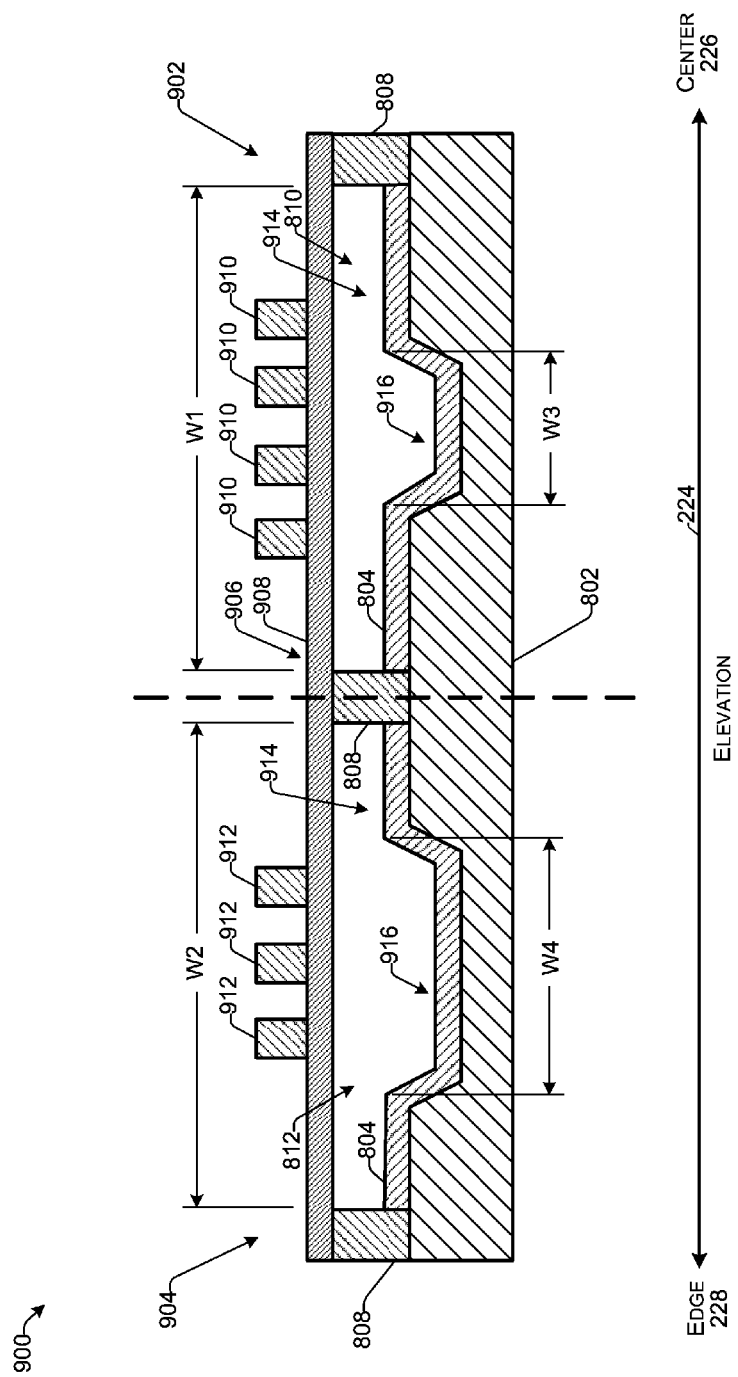
FIG. 9 illustrates an alternative configuration of a cross-sectional view of two CMUT cells having different frequencies and cavity profiles according to some implementations.

FIG. 9 illustrates an alternative configuration of a cross-sectional view 900 of two CMUT cells having different frequencies according to some implementations. For example, a first CMUT cell 902 may correspond to a CMUT cell having a higher resonant frequency and a second CMUT cell 904 may correspond to a CMUT cell having a lower resonant frequency than the first CMUT cell 902. Further, the two CMUT cells illustrated in FIG. 9 may not necessary be adjacent cells. The relationship between the two cells may generally be described as: a first CMUT cell with higher frequency is closer to the center 226 of the CMUT array, and a second CMUT cell with lower frequency is closer to the edge 228 of the CMUT array (or edge 230 in other examples).

The CMUT cells 902 and 904 may be constructed similarly to the CMUT cells 604, 702, and 608, 704, respectively, discussed above with respect to FIG. 8, and may include the substrate 802, the optional insulation layer 804, the sidewalls 808, a first cavity 810, and a second cavity 812. Furthermore, in this example, the width W1 of the first cavity 810 may be equal to the width W2 of the second cavity 812, and the lengths of the cavities 810 and 812 in the lateral direction may also be the same.

A membrane 906 may include a first layer 908 that may be made of single layer or multiple layers, with at least one layer of conductive material to serve as a second electrode. The first layer 908 may extend to contact the sidewalls 808 and, in some examples, may serve to seal the cavities 810 and 812 of the CMUT cells 902 and 904, respectively. In this example, the membrane 906 further includes a first patterned layer 910 formed over the first cavity 810, and a second pattern layer 912 formed over the second cavity 812. The patterned layers 910 and 912 make the membrane 906 non-uniform over the first cavity 810 and the second cavity 812. Accordingly, the configuration of the patterned layers 910 and 912 may be controlled to control the mechanical properties (e.g., the frequency, equivalent spring constant, etc.) of the membrane 906 over the first cavity 810 and the second cavity 812. For instance, the pattern of the first patterned layer 910 may be designed to enable the first CMUT cell 902 to resonate at a higher frequency than the resonant frequency of the second CMUT cell 904 having the second patterned layer 912 formed thereon. As one example, the patterned layer 910 may make the portion of the membrane 906 over the first cavity 810 stiffer than the portion of the membrane 906 over the second cavity 812 having the second patterned layer 912.

There are many pattern configurations that may be used to attain various levels of flexibility and or mass of the membrane 906 over the first cavity 810 and the second cavity 812. Some non-limiting examples of patterns that may be used for the layers 908, 910 and/or 912 for controlling membrane properties are described in U.S. Pat. No. 8,483,014, entitled "Micromachined Ultrasonic Transducers", issued to Yongli Huang on Jul. 9, 2013, which is incorporated herein by reference. In addition, both the first layer 908 and/or the patterned layers 910 and 912 may be designed differently to achieve the different frequencies of the CMUT cells 902 and 904, and/or one portion of the membrane might not be patterned.

In addition, the collapse voltages of the CMUT cells 902 and 904 with different frequencies may be designed to be similar. For example, the collapse voltages of the CMUT cells 604, 702, 902 and 608, 704, 904, respectively, may be designed to be within a 15% variation as to the collapse voltages. For instance, similar collapse voltages of the CMUT cells with different membrane properties may be achieved by using different cavity depths and shapes. Several example cavity configurations are shown in FIGS. 8 and 9. For example, in FIG. 8, the first cavity 810 has a depth D1 that is less than the depth D2 of the second cavity 812. Thus, for the smaller membrane area, the depth D1 is shallower than the depth D2 corresponding to a larger membrane dimension.

As another example, in FIG. 9, the cavities 810 and 812 have first regions 914 with a first depth and second regions 916 with a second, deeper depth, which may be made by forming steps on the substrate 802. The relative widths W3 and W4 of the second region 916 may be different between the first CMUT cell 902 and the second CMUT cell 904 so that a similar voltage level may have different electrical field in cavities 810 and 812 to achieve desired collapse voltages for each cell despite a difference in stiffness between cells. For example, two cells with the different membrane stiffness can have the similar collapse voltage. In some examples, the CMUT cells herein may include cavities formed with more than two regions having different depths and widths to achieve desired cavity profile, which generates the different electrical field in the cavities in different cells. Accordingly, the structures illustrated in FIGS. 8 and 9 may be used to control the electrical fields for achieving desired collapse voltages for the respective CMUT cells.

In addition, in some examples of a CMUT array herein, the CMUT cells closer to the center may have higher transducing efficiency than the CMUT cells closer to the edge along the elevation direction to achieve desired apodization profiles. For example, the transducing efficiency of a CMUT cell may be determined at least in part on the electrical field between two electrodes of a CMUT cell. For example, a higher electrical field may result in a higher transducing efficiency. For a given applied voltage, the electrical field may be determined by the cavity depths and shapes of the respective CMUT cells. Accordingly, the cell structures illustrated in FIGS. 8 and 9 may also be used to achieve differences in electrical field between two electrodes for different CMUT cells in the CMUT array 102.

Figure 10:
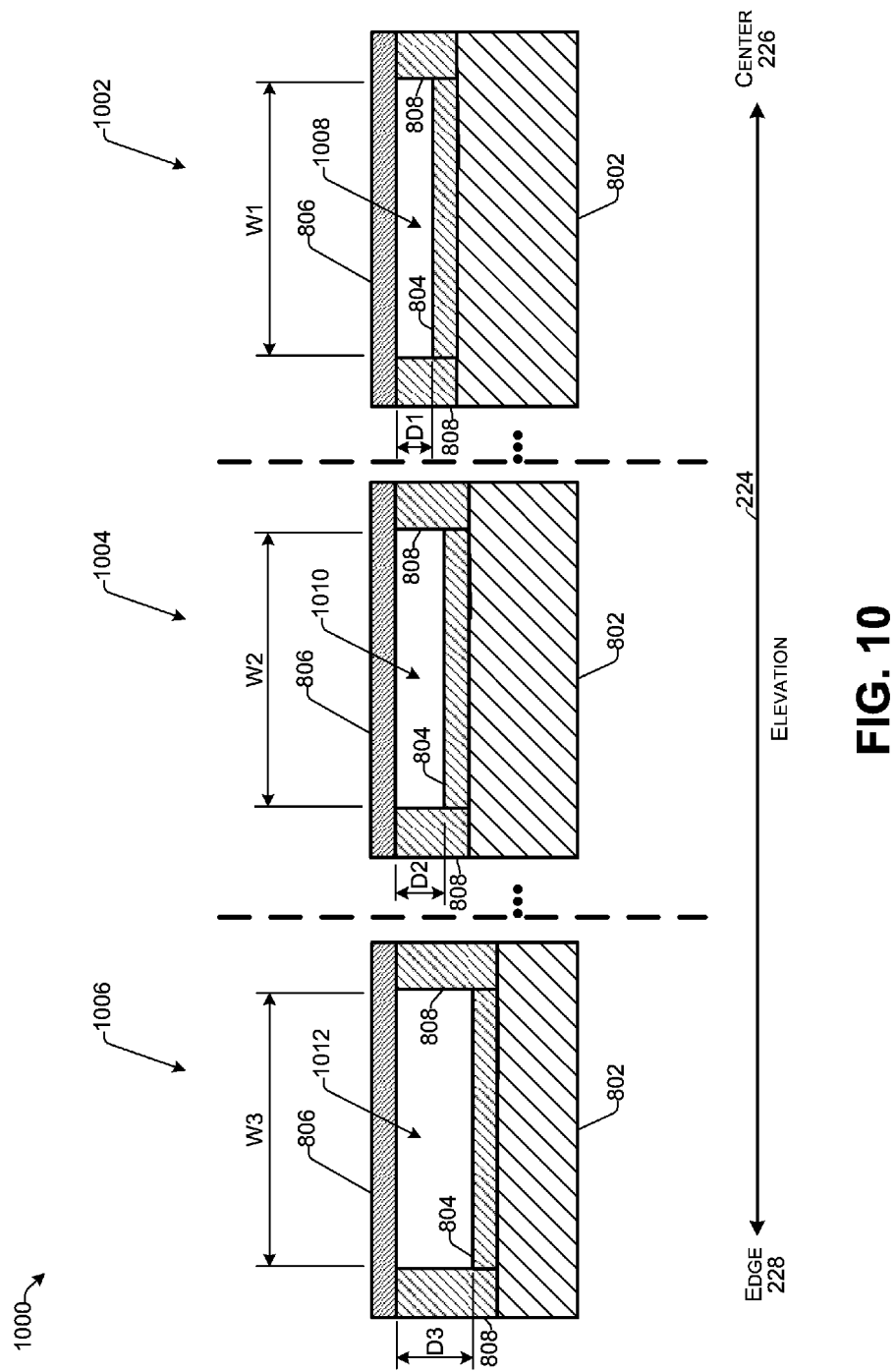
FIG. 10 illustrates an example of varying cavity profile of CMUT cells from the center toward the edges to achieve varying performance (e.g., transmit power, receive sensitivity, or/and frequency, etc.) according to some implementations.

FIG. 10 illustrates an example 1000 of varying cell configurations to achieve a higher transducing efficiency for CMUT cells that are closer to the center 226, and lower transducing efficiency for CMUT cells that are closer to the edge 228 and farther from the center 226. In the example of FIG. 10, a first CMUT cell 1002 is closer to the center 226, a second CMUT cell 1004 is farther from the center 226 than the first CMUT cell 1002, and a third CMUT cell 1006 is farther from the center 226 and closer to the edge 228 than the first CMUT cell 1002 and the second CMUT cell 1004. The first CMUT cell 1002 has a first cavity 1008 having a first depth D1, the second CMUT cell 1004 has a second cavity 1010 having a second depth D2, and the third CMUT cell 1006 has a third cavity 1012 having a third depth D3. The CMUT cells 1002-1006 in this example may correspond to any group of CMUT cells discussed above and are not necessarily immediately adjacent to each other.

In this example, the three CMUT cells 1002-1006 may have substantially identical structures. The membrane 806 dimensions of the structures can be designed to be different or the same. For example, if the cells have different dimensions (e.g., W1≠W2≠W3), then the resonant frequencies of the CMUT cells may be different. The CMUT cells closer to the center 226 in the elevation direction 224 may typically be designed to have a higher resonant frequency than the CMUT cells closer to the edge. In other examples, the CMUT cells may have the same resonant frequencies, the respective widths of the cavities 1008-1012 may be the same, i.e., W1=W2=W3. Similarly, the respective lengths (not shown in FIG. 10) of the cavities 1008-1012 may be the same.

In the illustrated example, the respective depths D1-D3 of the respective cavities 1008-1012 increase from the center 226 toward the edge 228. Accordingly, the respective transducing gaps between electrodes (e.g., a bottom electrode on or corresponding to the substrate 802, and a top electrode on or corresponding to the membrane 806) vary as defined by the different cavity depths, i.e., D3>D2>D1. For a given (or the same) applied voltage, the narrower the transducing gap (i.e., the smaller the depth), the higher the electrical field and the greater the transducing efficiency of the corresponding CMUT cell. Therefore, the transducing efficiency of the first CMUT cell 1002 is higher than that of the second CMUT cell 1004 and the third CMUT cell 1006. Similarly, the transducing efficiency of the second CMUT cell 1004 is higher than that of the third CMUT cell 1006. Furthermore, in some examples, two or more of the CMUT cells 1002-1006 may be in different regions of the same sub-element, rather than in different sub-elements.

Figure 11:
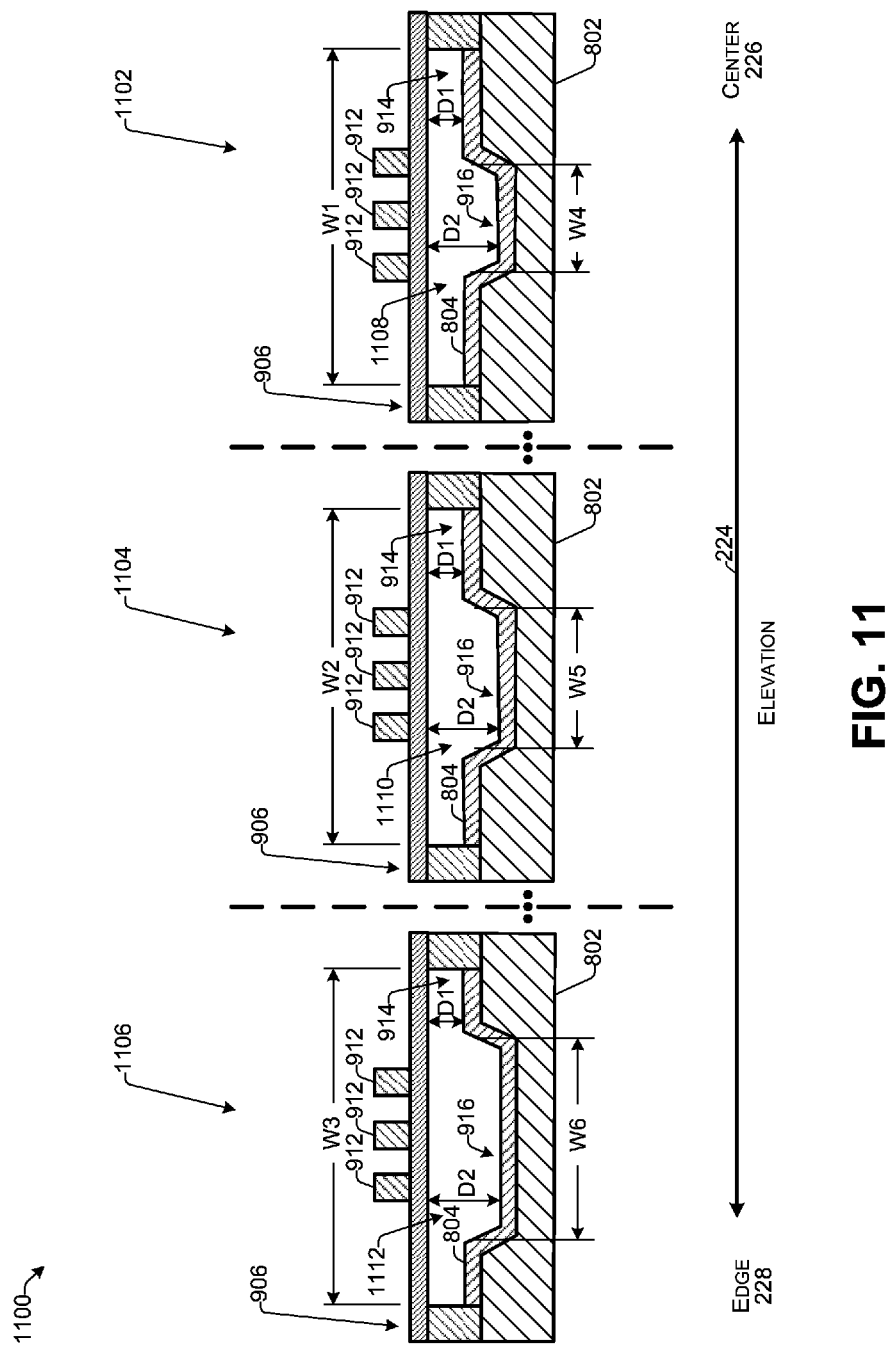
FIG. 11 illustrates an example of varying cavity profile of CMUT cells from the center toward the edges to achieve varying performance (e.g., transmit power, receive sensitivity, or/and frequency, etc.) according to some implementations.

FIG. 11 illustrates an example 1100 of varying cell configurations to achieve a higher transducing efficiency for CMUT cells that are closer to the center 226, and lower transducing efficiency for CMUT cells that are closer to the edge 228 and farther from the center 226. In the example of FIG. 11, a first CMUT cell 1102 is closer to the center 226, a second CMUT cell 1104 is farther from the center 226 than the first CMUT cell 1002, and a third CMUT cell 1106 is farther from the center 226 and closer to the edge 228 than the first CMUT cell 1102 and the second CMUT cell 1104. The first CMUT cell 1102 has a first cavity 1108, the second CMUT cell 1104 has a second cavity 1110, and the third CMUT cell 1106 has a third cavity 1112. The CMUT cells 1102-1106 in this example may correspond to any group of CMUT cells discussed above and are not necessarily immediately adjacent to each other. Additionally, the cavities 1108-1112 may have a varied depth of at least two different levels. Thus, each of the cavities 1108-1112 has a first region 914 with a first depth D1 and a second region 916 with a second, deeper depth D2, which may be made by forming steps on the substrate 802.

In the example of FIG. 11, the three CMUT cells 1102-1106 may have different or substantially identical structures in several dimensions. The dimensions of the membrane structures, 906 and 912, can be designed to be different or the same to provide the different or the same resonant frequencies. For example of the CMUT cells having different resonant frequencies, the CMUT cells may have different respective widths of the cavities (e.g. W1≠W2≠W3), or other features, such as the layer 912, may be different, or both. Thus, the resonant frequencies of the CMUT cells may be different. The CMUT cells closer to the center 226 in the elevation direction 224 may typically be designed to have a higher resonant frequency than those closer to the edge. In other examples, such as when the cells have the same resonant frequencies, the respective widths of the cavities 1108-1112 may be the same, i.e., W1=W2=W3. Similarly, the respective lengths (not shown in FIG. 11) of the cavities 1108-1112 may be the same. Further, the respective patterned layers 912 on the respective membranes 906 may be the same.

Regardless of whether the dimensions of the membrane structures 906 and 912 of the three CMUT cells 1102-1106 are the same or not, the first depth D1 and the second depth D2 of the respective cavities 1108-1112 may also be the same. However, in this example, the three CMUT cells 1102-1106 have respective regions 916 of different widths that increase in width from the center 226 toward the edge 228. For example, the width W4 of the region 916 of the first CMUT cell 1102 is smaller than the widths W5 of the region 916 of the second CMUT cell 1104 and the width W6 of the region 916 of the third CMUT cell 1106, i.e., W6>W5>W4. Accordingly, for a given (or the same) applied voltage, the electrical field at region 916 of the third CMUT cell 1106 having the width W6 is weaker than the electrical field at the region 916 of the second CMUT cell 1104 and the first CMUT cell 1102, which have smaller widths W5 and W4, respectively. Thus, the CMUT cell 1106 with the wider D2 region 916 (having width W6) has a weaker overall electrical field (or average electrical field) than the second CMUT cell 1104 with the narrower D2 region 916 (having width W5), which in turn, has a weaker overall electrical field (or average electrical field) than the first CMUT cell 1102 with the still narrower D2 region 916 (having width W4). Therefore, the transducing efficiency of CMUT cell 1106 is lower than the transducing efficiency of the CMUT cell 1104, which is lower than the transducing efficiency of the CMUT cell 1102. In other words, since W6>W5>W4, therefore the transducing efficiency of the CMUT cells increases from the edge 228 to the center 226. Additionally, in some examples, two or more of the CMUT cells 1102-1106 may be in different regions of the same sub-element, rather than in different sub-elements. Furthermore, while several example cavity configurations have been described herein, numerous other configurations will be apparent to those of skill in the art having the benefit of the disclosure herein.

Figure 12:
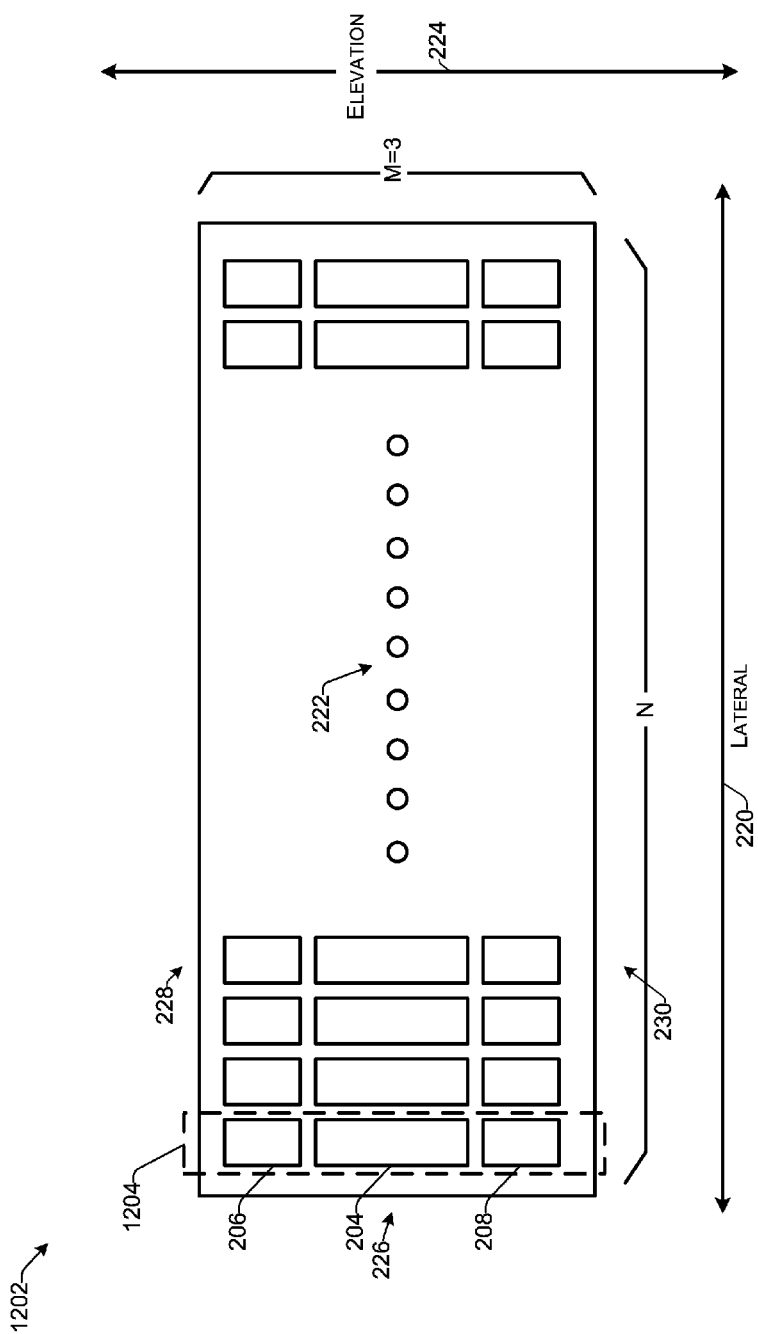
FIG. 12 illustrates an example of a CMUT array with three sub-elements in the elevation dimension according to some implementations.

FIG. 12 illustrates an example implementation of a CMUT array 1202 in which each CMUT element 1204 has three sub-elements in the elevation direction 224 according to some implementations. In some examples, the CMUT array 1202 may correspond to the CMUT array 102 and may be used in the system of FIG. 1. As illustrated in FIG. 12, the three sub-elements include the center sub-element 204 and a first adjacent sub-element 206 and a second adjacent sub-element 208 symmetrically arranged around the center sub-element 204. In this example, the first adjacent sub-element 206 and the second adjacent sub-element 208 may be electrically connected to each other to enable treatment as a single sub-element. As discussed above, the center frequencies of the sub-elements 204, 206, and 208 may decrease in the elevation direction 224 from the center 226, toward the edges 228 and 230, respectively. Further, in this example, all three sub-elements 204, 206, and 208 are rectangular.

Figure 13:
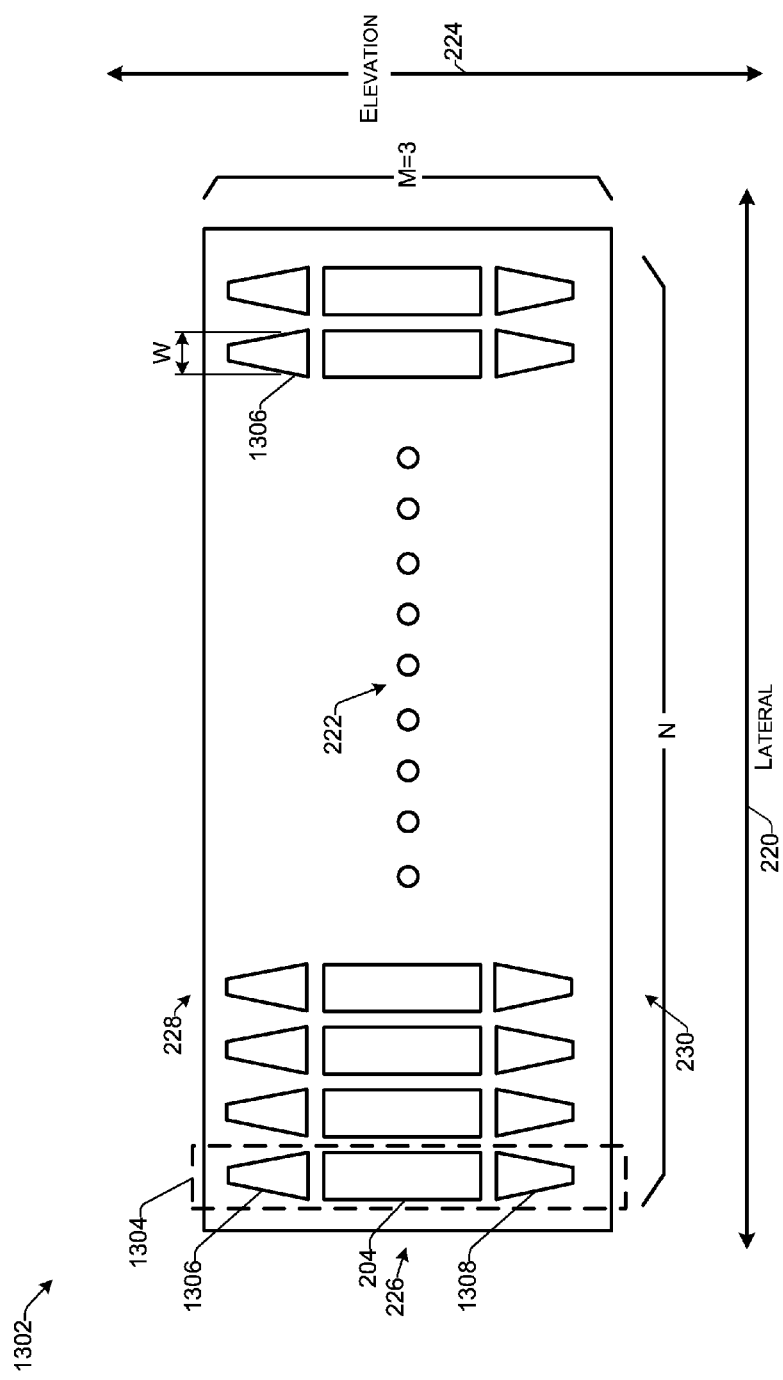
FIG. 13 illustrates an example of a CMUT array with three sub-elements in the elevation dimension according to some implementations.

FIG. 13 illustrates an example CMUT array 1302 with three sub-elements in the elevation dimension 224 according to some implementations. In some examples, the CMUT array 1302 may correspond to the CMUT array 102 and may be used in the system of FIG. 1. The CMUT array 1302 includes a plurality of N elements 1304. Each element 1304 includes the center sub-element 204 and two adjacent sub-elements 1304 and 1306, which are symmetrically disposed on either side of the center sub-element 204 in the elevation dimension 224. In this example, the two adjacent sub-elements 1304 and 1306 are trapezoidal in shape when viewed in plan, while the center sub-element 204 remains rectangular.

In the example of FIG. 13, each element 1304 includes the symmetrically disposed trapezoidal sub-elements 1306 and 1308 that decrease in width W as the sub-elements 1306 and 1308 approach the respective edges 228 and 230 of the CMUT array 1302. Thus, the trapezoidal shape of the sub-elements 1306 and 1308 causes the active area of the sub-elements 1306 and 1308 to decrease towards the edges 228 and 230, and therefore creates a linear apodization profile. An apodization profile is a window function that weighs more in the center and less toward both edges. In ultrasound imaging, apodization may be utilized to shape ultrasound beam patterns and reduce side lobe levels for obtaining better image quality. For instance, the center sub-element 204 at the center 226 of the array 1302 may vibrate more intensely than the sub-elements 1306 and 1308 near the edge of the array 1302, which may generate acoustic fields with minimum side lobes. Of course, both center and adjacent sub-elements may be formed having other shapes able to generate a desired apodization profile. Beside the shape variations, the cell density of each sub-element or region within a sub-element may change from the center 226 to the edges 228 and 230. For example, the cell density may decrease monotonically from the center 226 to the edges 228 and 230 to generate a desired apodization profile in the elevation dimension.

Figure 14:
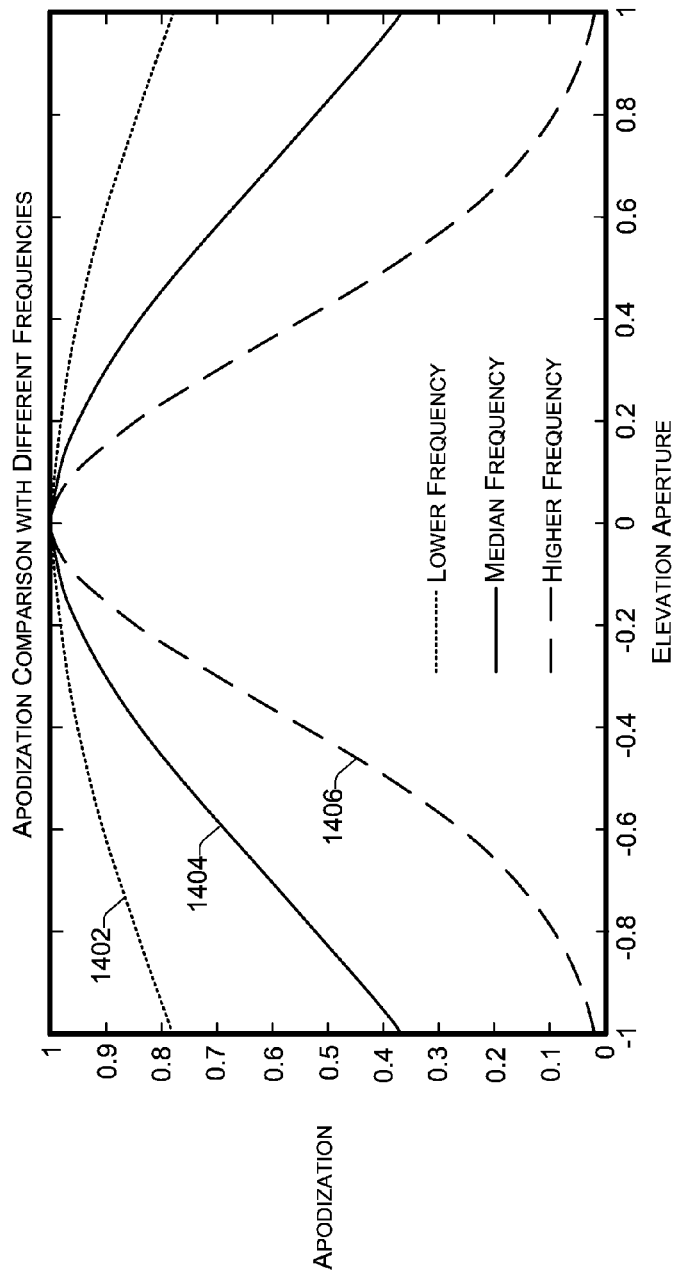
FIG. 14 illustrates a graph showing three example apodization profiles corresponding to different operating frequencies according to some implementations.

FIG. 14 illustrates a graph 1400 showing three example apodization profiles corresponding to different operating frequencies according to some implementations. The graph 1400 illustrates three different apodization profiles for a corresponding elevation aperture that may be generated with different operating frequencies of the CMUT arrays 102, 1302 herein. When operated at lower frequency, the center portion of a CMUT array is less sensitive while the edge portion is more sensitive, which results in a mild apodization profile as illustrated by the dotted line 1402. As the operating frequency increases to a median frequency, the center portion of the CMUT array becomes more sensitive while the edge portion become less sensitive, as illustrated by the solid line 1404. Further, as the operating frequency increases to a higher frequency, the center portion becomes even more sensitive, while the edge portions become even less sensitive, which results in an aggressive apodization profile as illustrated by dashed line 1406.

Figure 15:
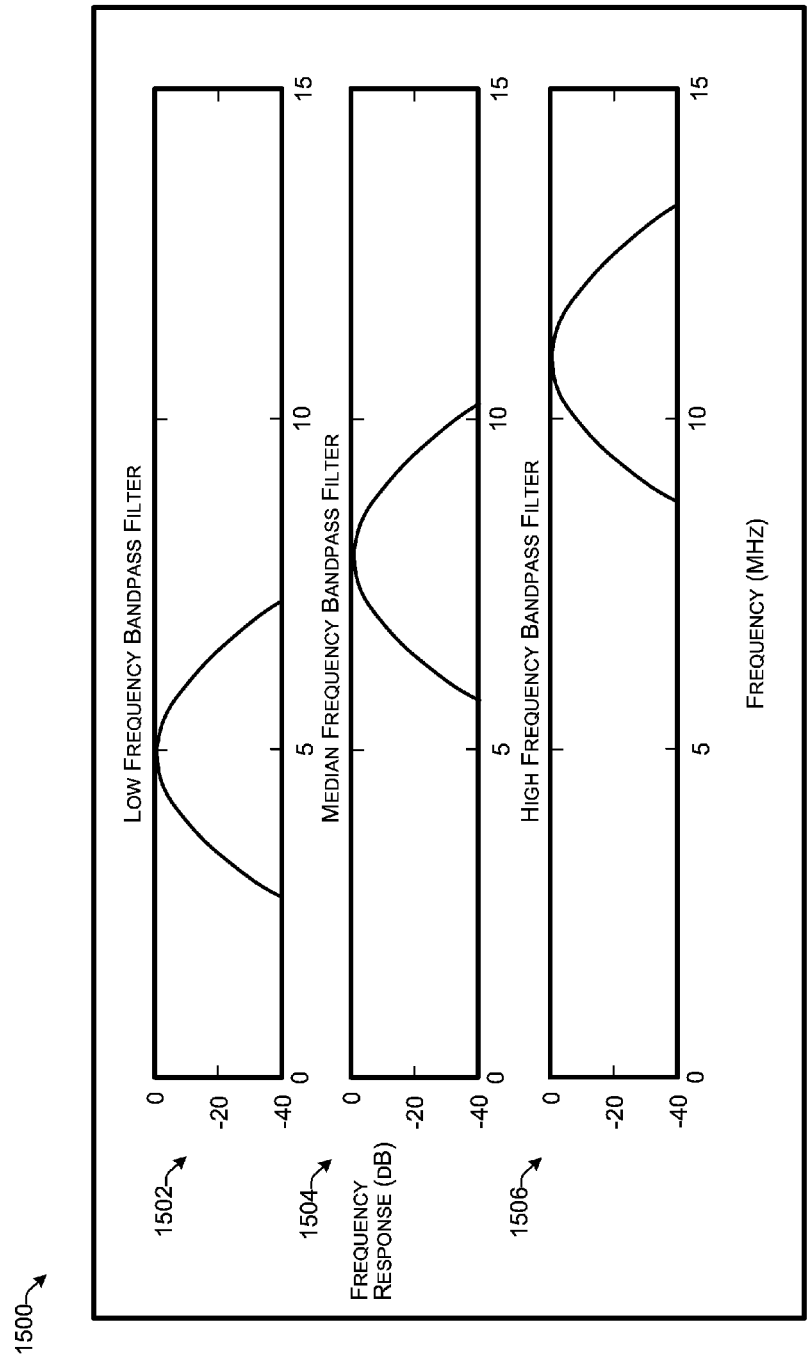
FIG. 15 is a set of three graphs illustrating example frequency responses of three bandpass filters, respectively, according to some implementations.

FIG. 15 is a set of three graphs 1500 illustrating example frequency responses of three bandpass filters according to some implementations. In the example of FIG. 15, a high frequency bandpass filter may be used in the near field, while a low frequency bandpass filter may be used in the far field in receive phase, while a median frequency bandpass filter may be used in between. Thus a first graph 1502 illustrates an example of frequency response vs. frequency for a low frequency bandpass filter; a second graph 1504 illustrates an example of frequency response vs. frequency for a median frequency bandpass filter; and a third graph 1506 illustrates an example of frequency response vs. frequency for a high frequency bandpass filter. The operating frequency selection may be accomplished by using the different low, median and high bandpass filters, such as may be included in the filter bank 106 discussed above with respect to FIG. 1. For example, a respective filter may be applied for filtering electrical transmission pulses based at least in part on a desired depth of imaging.

In some implementations, the transmit bandpass filters may be implemented digitally with a waveform generator. Alternatively in other implementations, the transmit bandpass filters may be implemented with analog components including capacitors, inductors, and resistors. In some cases, the receive bandpass filters may be implemented digitally with a set of matching filters whose center frequency downshifts with penetration depth. Additionally, or alternatively, the receive bandpass filters may be implemented using a lowpass filter combined with frequency dependent demodulation. In any event, implementations herein combine filtering with frequency-varied sub-elements to generate desired apodization profiles to provide ultrasound imaging that is able to operate at ultra-wide bandwidths and various operating frequencies.

Figure 16:
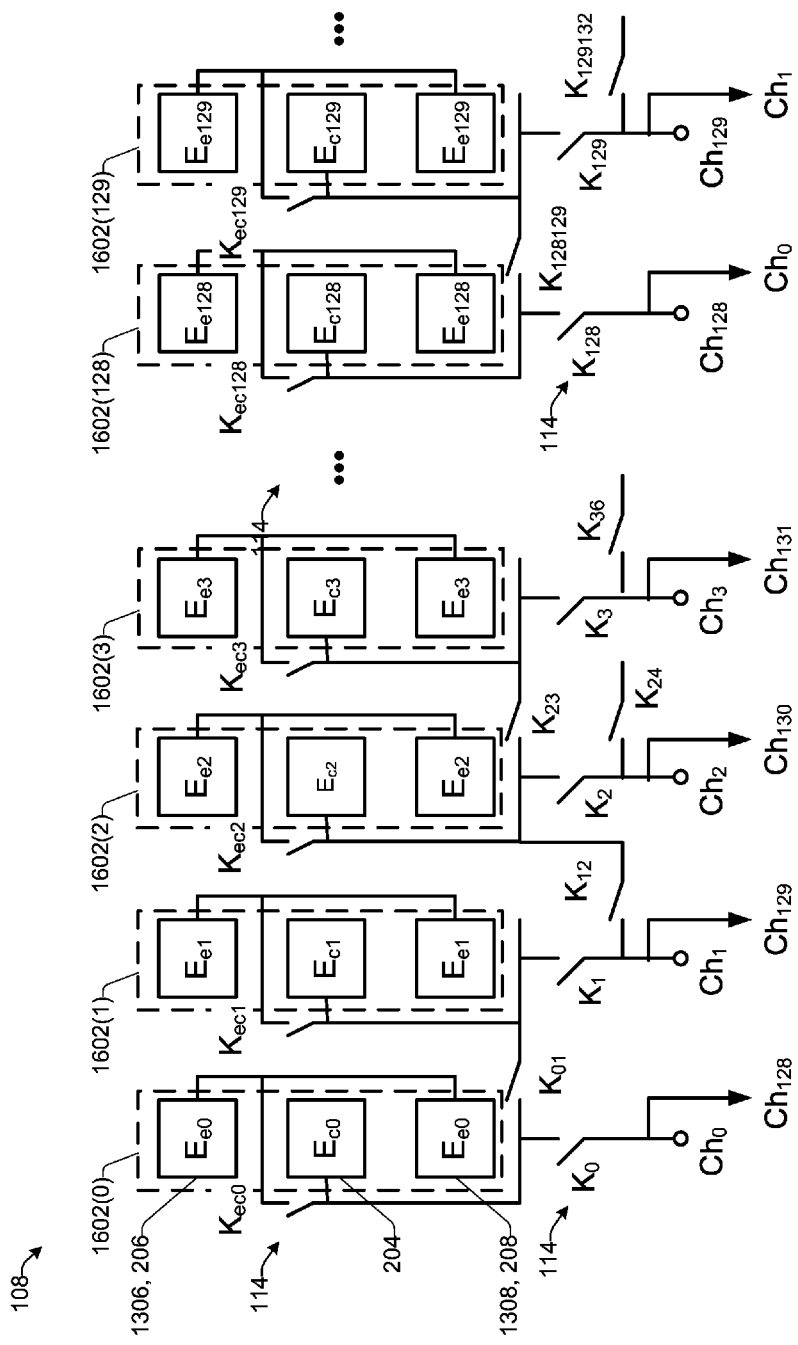
FIG. 16 illustrates an example of a multiplexer for selecting desired sub-elements according to some implementations.

FIG. 16 illustrates an example of the multiplexer 108 for selecting desired sub-elements according to some implementations. In the example of FIG. 16, the multiplexer 108 includes multiple high voltage analog switches 114, which are controlled by the imaging system 104, as discussed above with respect to FIG. 1. The system in this example may have 128 channels and the CMUT array may include 3×256 sub-elements (i.e., M=3 and N=256). In some examples, the CMUT array of FIG. 16 may correspond to the CMUT arrays 1202 and 1302 discussed above with respect to FIGS. 12 and 13, respectively. In other examples, M may be more than 3, such as discussed above with respect to the CMUT array 102 of FIG. 2. FIG. 16 illustrates the multiplexor switching for the first four elements 1602(0), 1602(1), 1602(2), and 1602(3), and for elements 1602(128) and 1602(129). Each element 1602 may include a center sub-element, e.g., center sub-element 204 ($E_c$) and two adjacent or edge sub-elements ($E_e$) such as elements 206 or 1306 and elements 208 or 1308, respectively.

For high frequency imaging, a Channel 0 may be connected to either Element 0 1602(0) if $K_0$ is on and $K_{128}$ is off, or Element 128 1602(128) if $K_{128}$ is on and $K_0$ is off; a Channel 1 may be connected to either Element 1 1602(1) if $K_1$ is on and $K_{129}$ is off, or Element 129 1602(129) if $K_{129}$ is on and $K_1$ is off, and so forth. Channel 0 is connected to both Element 0 1602(0) and Element 1 1602(1) if $K_{01}$ is on and $K_1$ is off; Channel 1 may be connected to both Element 2 1602(2) and Element 3 1602(3) if $K_{12}$ and $K_{23}$ are on and $K_1$ and $K_2$ are off, and so forth. For near field imaging, only center sub-elements 204 are connected to corresponding channels. For far field imaging, all three sub-elements 204 and 206, 1306 and 208, 1308, respectively are connected to corresponding channels when $K_{ec0}$, $K_{ec1}$, $K_{ec2}$, $K_{ec3}$, . . . $K_{ec128}$, $K_{ec129}$, . . . are on.

Although 128 channels, 256 elements, and 3 sub-elements are described here, the examples herein may be used for any number of channels, any number of elements, and any number of sub-elements. In general, the system can have N channels, the CMUT array can have k×M×N sub-elements, where N and k are positive integers, and M is a positive odd integer.

Further, through use of the multiplexor 108, the system 100 in FIG. 1 can choose a subset or all of k×M sub-elements to generate desired images based on imaging requirements, such as lateral resolution, elevation resolution, penetration, and field of view. The system 100 can also choose different apodization profiles in the elevation dimension using different filters to improve imaging performance, such as discussed above with respect to FIG. 15.

Figure 17:
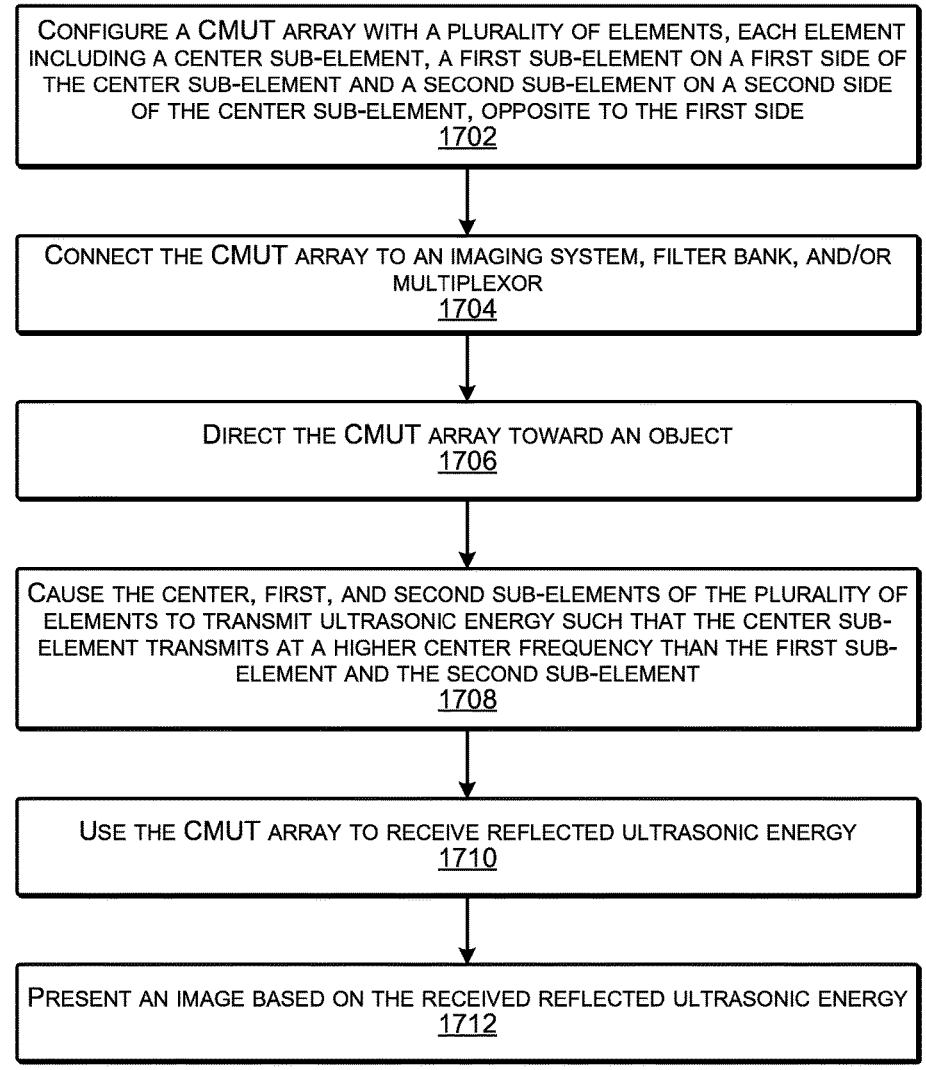
FIG. 17 is a flow diagram illustrating an example process according to some implementations.

FIG. 17 is a flow diagram illustrating an example process according to some implementations. The process is illustrated as collections of blocks in a logical flow diagram, which represents a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks may be combined in any order and/or in parallel to implement the process, or alternative processes, and not all of the blocks need be executed. For discussion purposes, the process is described with reference to the apparatuses, architectures and systems described in the examples herein, although the process may be implemented in a wide variety of other apparatuses, architectures and systems.

FIG. 17 is a flow diagram illustrating an example process 1700 according to some implementations.

At 1702, a CMUT array may be configured with a plurality of elements, each element including a center sub-element, a first sub-element on a first side of the center sub-element, and a second sub-element on a second side of the center sub-element, opposite to the first side. Further, in some cases, additional sub-elements may be included in each element, such as, for each element, a third sub-element on a side of the first sub-element opposite to the center sub-element, and a fourth sub-element, on a side of the second sub-element opposite to the center sub-element. Additional sub-elements may also be included in the CMUT array.

At 1704, the CMUT array may be connected to an imaging system, filter bank, and/or multiplexor. In some cases, the CMUT array may be included in a probe that includes or is connected to the imaging system, filter bank, and/or multiplexor.

At 1706, the CMUT array is directed toward an object. For example, for medical imaging, the CMUT array may be directed toward human tissue.

At 1708, a processor in the system may cause the center, first, and second sub-elements of each of the plurality of elements to transmit ultrasonic energy such that the center sub-element transmits at a higher center frequency than the first sub-element and the second sub-element. For instance, the center frequency may decrease toward the edges of the array in the elevation direction.

At 1710, the CMUT array may receive reflected ultrasonic energy. For example, the CMUT array may serve to receive ultrasound signals for imaging in addition to transmitting the ultrasound signals.

At 1712, the system may be present an image based on the received reflected ultrasound energy. For instance, the system may include one or more processors that process the received ultrasound energy and present an image on a display based on processing of the received ultrasound signal.

The example processes described herein are only examples of processes provided for discussion purposes. Numerous other variations will be apparent to those of skill in the art in light of the disclosure herein. Further, while the disclosure herein sets forth several examples of suitable systems, architectures and apparatuses for executing the processes, implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Various instructions, methods, and techniques described herein may be considered in the general context of computer-executable instructions, such as program modules stored on computer-readable media, and executed by the processor(s) herein. Generally, program modules include routines, programs, objects, components, data structures, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A system comprising:
    a capacitive micromachined ultrasound transducer (CMUT) array having a plurality of CMUT elements, individual ones of the CMUT elements including:
        a first sub-element;
        a second sub-element; and
        a third sub-element between the first sub-element and the second sub-element;
        wherein the third sub-element is configured to transmit ultrasonic energy at a higher center frequency than at least one of the first sub-element or the second sub-element.

2. The system as recited in claim 1, wherein the third sub-element comprises a first region including a plurality of first CMUT cells having a first resonant frequency and a second region including a plurality of second CMUT cells having a second resonant frequency that is different from the first resonant frequency.

3. The system as recited in claim 1, wherein the first sub-element and the second sub-element are electrically connected to each other and each include a plurality of regions, wherein:
    a first region includes a plurality of first CMUT cells having a first resonant frequency; and
    a second region includes a plurality of second CMUT cells having a second resonant frequency that is less than the first resonant frequency.

4. The system as recited in claim 3, wherein the second CMUT cells differ from the first CMUT cells by at least one of:
    a different shape when viewed in plan;
    a different membrane thickness;
    a different pattern formed on at least respective membranes of at least one of the first CMUT cells or the second CMUT cells; or
    cavities of the second CMUT cells have a larger area than cavities of the first CMUT cells.

5. The system as recited in claim 1, wherein there are a plurality of sub-elements in the individual elements in addition to the first sub-element, the second sub-element, and the third sub-element, the system further comprising:
    one or more processors; and
    one or more computer-readable media storing instructions executable by the one or more processors, wherein the instructions program the one or more processors to:
        determine a first plurality of the sub-elements to transmit ultrasonic energy from the CMUT array; and
        control a first plurality of switches of a multiplexor for causing the first plurality of sub-elements to transmit the ultrasonic energy.

6. The system as recited in claim 5, wherein the instructions further program the one or more processors to:
    determine a second plurality of the sub-elements to transmit ultrasonic energy for increasing an aperture of the CMUT array; and
    control a second plurality of switches of the multiplexor for causing the second plurality of sub-elements to transmit the ultrasonic energy.

7. The system as recited in claim 5, wherein the instructions further program the one or more processors to apply at least one filter for filtering ultrasonic energy based at least in part on a depth of imaging.

8. The system as recited in claim 5, wherein the instructions further program the one or more processors to apply at least one filter for filtering electrical transmission pulses based at least in part on a depth of imaging.

9. The CMUT element as recited in claim 1, wherein:
    the first sub-element includes one or more first CMUT cells;
    the second sub-element includes one or more second CMUT cells; and
    the third sub-element includes one or more third CMUT cells, wherein the one or more third CMUT cells have a respective cavity shape per CMUT cell that is different from a respective cavity shape per CMUT cell of at least one of the first CMUT cells or the second CMUT cells so that a transducing efficiency of the third CMUT cells is higher than a transducing efficiency of the at least one of the first CMUT cells or the second CMUT cells for a same applied voltage.

10. A CMUT element comprising:
    a first sub-element having one or more first CMUT cells; and
    a second sub-element having one or more second CMUT cells;
    wherein the one or more first CMUT cells have a resonant frequency different from a resonant frequency of the one or more second CMUT cells,
    wherein the one or more first CMUT cells are disposed laterally with respect to the one or more second CMUT cells so that one or more membranes of the one or more first CMUT cells are co-planar with one or more membranes of the one or more second CMUT cells.

11. The CMUT element as recited in claim 10, wherein:
    the first sub-element includes a plurality of the first CMUT cells disposed in a plurality of regions;
    a first region of the plurality of regions includes a first subset of the first CMUT cells; and
    a second region of the plurality of regions includes a second subset of the first CMUT cells; and the first subset of the first CMUT cells has a resonant frequency that is greater than a resonant frequency of the second subset of the first CMUT cells.

12. The CMUT element as recited in claim 11, wherein:
a third region of the first sub-element includes a third subset of the first CMUT cells;
the first CMUT cells of the first subset have a resonant frequency that is greater than the resonant frequency of the first CMUT cells of the second subset and a resonant frequency of the first CMUT cells of the third subset; and
the second region is disposed on one side of the first region and the third region is disposed on an opposite side of the first region.

13. The CMUT element as recited in claim 11, wherein the resonant frequency of the CMUT cells of the second subset is a higher frequency than the resonant frequency of the second CMUT cells of the second sub-element.

14. The CMUT element as recited in claim 10, wherein the one or more first CMUT cells have respective membranes that differ from respective membranes of the one or more second CMUT cells by at least one of:
membrane thickness of the respective membranes; or
having a patterned layer formed on at least one the respective membranes of the one or more first CMUT cells or the respective membranes of the one or more second CMUT cells.

15. The CMUT element as recited in claim 10, wherein the one or more first CMUT cells have a membrane area per CMUT cell that is different from a membrane area per CMUT cell of the one or more second CMUT cells.

16. The CMUT element as recited in claim 10, wherein the one or more first CMUT cells have a respective cavity shape per CMUT cell that is different from a respective cavity shape per CMUT cell of the one or more second CMUT cells so that a collapse voltage associated with the one or more first CMUT cells within 15% of a collapse voltage associated with the one or more second CMUT cells.

17. The CMUT element as recited in claim 10, wherein the one or more first CMUT cells have a respective cavity shape per CMUT cell that is different from a respective cavity shape per CMUT cell of the one or more second CMUT cells so that a transducing efficiency of the one or more first CMUT cells is higher than a transducing efficiency of the one or more second CMUT cells for a same applied voltage.

18. The CMUT element as recited in claim 10, wherein the one or more first CMUT cells have a higher resonant frequency than the one or more second CMUT cells and the first sub-element is disposed closer to a center of the CMUT element than the second sub-element so that a center frequency associated with the CMUT element is higher near a center of the CMUT element and decreases toward an edge of the CMUT element in an elevation direction.

19. The CMUT element as recited in claim 10, further comprising a third sub-element disposed on a side of the first sub-element opposite from the second sub-element, wherein the third sub-element includes a plurality of third CMUT cells having a resonant frequency different from the resonant frequency of the one or more first CMUT cells.

20. A method comprising:
directing a capacitive micromachined ultrasound transducer (CMUT) array toward an object, the CMUT array including a plurality of elements, each element including at least a first sub-element, a second sub-element and a third sub-element, wherein the first sub-element is on a first side of the third sub-element and the second sub-element on a second side of the third sub-element, opposite to the first side; and
causing the first sub-element, the second sub-element, and the third sub-element to transmit ultrasonic energy, wherein the third sub-element transmits at a higher center frequency than the first sub-element and the second sub-element.

21. The method as recited in claim 20, wherein the first sub-element includes a plurality of first CMUT cells, the second sub-element includes a plurality of second CMUT cells, and the third sub-element includes a plurality of third CMUT cells, the first CMUT cells and the second CMUT cells having a lower resonant frequency than the third CMUT cells, wherein:
causing the first sub-element, the second sub-element, and the third sub-element to transmit ultrasonic energy comprises causing the first CMUT cells, the second CMUT cells, and the third CMUT cells to transmit the ultrasonic energy.

22. The method as recited in claim 20, wherein the CMUT array further includes, for each element, a fourth sub-element on a side of the first sub-element opposite to the third sub-element, and a fifth sub-element, on a side of the second sub-element opposite to the third sub-element, the method further comprising:
increasing an aperture by causing the first sub-element, the second sub-element, the third sub-element, the fourth sub-element, and the fifth sub-element to transmit ultrasonic energy, wherein the fourth sub-element transmits at a lower center frequency than the first sub-element and the fifth sub-element transmits at a lower center frequency than the second sub-element.

23. The method as recited in claim 22, wherein increasing the aperture further comprises sending at least one signal to a multiplexor to cause one or more switches associated with the multiplexer to connect the fourth sub-element and the fifth sub-element for causing the transmission of the ultrasonic energy.

24. The method as recited in claim 20, further comprising using a plurality of bandpass filters to determine, at least in part, the frequency of transmission of the ultrasonic energy by the elements of the CMUT array.

25. A CMUT element comprising:
a first sub-element having one or more first CMUT cells; and
a second sub-element having one or more second CMUT cells;
wherein the one or more first CMUT cells have a transducing efficiency different from a transducing efficiency of the one or more second CMUT cells.

26. The CMUT element as recited in claim 25, wherein the transducing efficiency comprises at least one of:
a transmission efficiency of respective CMUT cells; or
a receiving sensitivity of the respective CMUT cells.

27. The CMUT element as recited in claim 25, wherein:
the first sub-element includes a plurality of the first CMUT cells disposed in a plurality of regions;
a first region of the plurality of regions includes a first subset of the first CMUT cells;
a second region of the plurality of regions includes a second subset of the first CMUT cells; and
the first subset of the first CMUT cells has a transducing efficiency that is greater than a transducing efficiency of the second subset of the first CMUT cells.

28. The CMUT element as recited in claim 25, wherein the one or more first CMUT cells have a resonant frequency different from a resonant frequency of the one or more second CMUT cells.

29. The CMUT element as recited in claim 25, wherein the one or more first CMUT cells have a cavity shape that is different from a cavity shape of the one or more second CMUT cells to provide, at least in part, different respective transducing efficiencies.

* * * * *